United States Patent
Steger et al.

(10) Patent No.: US 11,129,683 B2
(45) Date of Patent: Sep. 28, 2021

(54) SYSTEMS AND METHODS FOR CONTROLLING A SURGICAL INSTRUMENT

(71) Applicant: INTUITIVE SURGICAL OPERATIONS, INC., Sunnyvale, CA (US)

(72) Inventors: John Ryan Steger, Sunnyvale, CA (US); Brian M. Crews, San Jose, CA (US); Craig R. Gerbi, Half Moon Bay, CA (US); Tyler J. Morrissette, Niantic, CT (US); Margaret M. Nixon, San Jose, CA (US); Joseph P. Orban, III, Norwalk, CT (US); Theodore W. Rogers, Alameda, CA (US); Alain Sadaka, San Jose, CA (US); Charles E. Swinehart, San Jose, CA (US); Michael Turner, Sunnyvale, CA (US); Kerry S. Wang, Saratoga, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 116 days.

(21) Appl. No.: 16/316,939

(22) PCT Filed: Jul. 14, 2017

(86) PCT No.: PCT/US2017/042204
§ 371 (c)(1),
(2) Date: Jan. 10, 2019

(87) PCT Pub. No.: WO2018/013965
PCT Pub. Date: Jan. 18, 2018

(65) Prior Publication Data
US 2020/0078109 A1    Mar. 12, 2020

Related U.S. Application Data

(60) Provisional application No. 62/362,406, filed on Jul. 14, 2016.

(51) Int. Cl.
*A61B 34/35* (2016.01)
*A61B 34/30* (2016.01)
(Continued)

(52) U.S. Cl.
CPC ............ *A61B 34/35* (2016.02); *A61B 1/3132* (2013.01); *A61B 17/4241* (2013.01);
(Continued)

(58) Field of Classification Search
USPC .......................................... 606/1
See application file for complete search history.

(56) References Cited

U.S. PATENT DOCUMENTS

| 3,858,578 A | 1/1975 | Milo et al. |
| 4,132,652 A | 1/1979 | Anderson et al. |

(Continued)

FOREIGN PATENT DOCUMENTS

| CN | WO-201412727 A1 | 8/2014 |
| CN | 104640515 A | 5/2015 |

(Continued)

OTHER PUBLICATIONS

Extended European Search Report for Application No. EP17828558.1 dated Feb. 13, 2020, 7 pages.

(Continued)

*Primary Examiner* — Nicole F Lavert
*Assistant Examiner* — Nicole F Johnson
(74) *Attorney, Agent, or Firm* — Artegis Law Group, LLP

(57) ABSTRACT

A teleoperational medical system comprises an input device and a manipulator configured to couple with and move an instrument. The system also comprises a control system including one or more processors. In response to a determination that the instrument is inserted into an instrument workspace in a corresponding direction to a field of view of the workspace, the control system is configured to map (Continued)

movement of the input device to movement of the instrument according to a first mapping. In response to a determination that the instrument is inserted into the instrument workspace in a non-corresponding direction to the field of view, the control system is configured to map movement of the input device to movement of the instrument according to a second mapping. The second mapping includes an inversion of the first mapping for at least one direction of motion of the instrument.

20 Claims, 17 Drawing Sheets

(51) Int. Cl.
    *A61B 90/00*         (2016.01)
    *A61B 1/313*         (2006.01)
    *A61B 17/42*         (2006.01)
    *A61B 17/00*         (2006.01)

(52) U.S. Cl.
    CPC .............. *A61B 2017/00477* (2013.01); *A61B 2034/302* (2016.02); *A61B 2090/3941* (2016.02); *A61B 2090/3945* (2016.02); *A61B 2090/3983* (2016.02)

(56) References Cited

U.S. PATENT DOCUMENTS

| | | | |
|---|---|---|---|
| 4,143,652 A | 3/1979 | Meier et al. |
| 4,767,231 A | 8/1988 | Wallis et al. |
| 4,775,362 A | 10/1988 | Kronner et al. |
| 4,924,851 A | 5/1990 | Ognier et al. |
| 5,047,036 A | 9/1991 | Koutrouvelis et al. |
| 5,170,790 A | 12/1992 | Lacoste et al. |
| 5,178,606 A | 1/1993 | Ognier et al. |
| 5,184,601 A | 2/1993 | Putman et al. |
| 5,351,676 A | 10/1994 | Putman et al. |
| 5,383,888 A | 1/1995 | Zvenyatsky et al. |
| 5,409,496 A | 4/1995 | Rowden et al. |
| 5,441,042 A | 8/1995 | Putman et al. |
| 5,445,643 A | 8/1995 | Valtchev et al. |
| 5,487,377 A | 1/1996 | Smith et al. |
| 5,520,698 A | 5/1996 | Koh et al. |
| 5,540,700 A | 7/1996 | Rowden et al. |
| 5,554,160 A | 9/1996 | Caillouette et al. |
| 5,556,401 A | 9/1996 | Caillouette et al. |
| 5,560,577 A | 10/1996 | Keselman et al. |
| 5,582,379 A | 12/1996 | Keselman et al. |
| 5,643,285 A | 7/1997 | Rowden et al. |
| 5,643,311 A | 7/1997 | Smith et al. |
| 5,681,325 A | 10/1997 | Hasson et al. |
| 5,782,859 A | 7/1998 | Nicholas et al. |
| 5,792,135 A | 8/1998 | Madhani et al. |
| 5,800,381 A | 9/1998 | Ognier et al. |
| 5,802,641 A | 9/1998 | Van et al. |
| 5,840,077 A | 11/1998 | Rowden et al. |
| 5,918,844 A | 7/1999 | Ognier et al. |
| 6,062,829 A | 5/2000 | Ognier et al. |
| 6,235,037 B1 | 5/2001 | East et al. |
| 6,248,101 B1 | 6/2001 | Whitmore, III et al. |
| 6,331,181 B1 | 12/2001 | Tierney et al. |
| 6,331,191 B1 | 12/2001 | Chobotov et al. |
| 6,423,075 B1 | 7/2002 | Singh et al. |
| 6,424,885 B1 | 7/2002 | Niemeyer et al. |
| 6,488,030 B1 | 12/2002 | Wardle et al. |
| 6,491,701 B2 | 12/2002 | Tierney et al. |
| 6,506,149 B2 | 1/2003 | Peng et al. |
| 6,514,239 B2 | 2/2003 | Shimmura et al. |
| 6,645,196 B1 | 11/2003 | Nixon et al. |
| 6,653,055 B1 | 11/2003 | Meier et al. |
| 6,663,055 B2 | 12/2003 | Boucher et al. |
| 6,699,235 B2 | 3/2004 | Wallace et al. |
| 6,716,163 B2 | 4/2004 | Muhanna et al. |
| 6,730,020 B2 | 5/2004 | Peng et al. |
| 6,817,974 B2 | 11/2004 | Cooper et al. |
| 6,949,105 B2 | 9/2005 | Bryan et al. |
| 7,066,926 B2 | 6/2006 | Wallace et al. |
| 7,125,380 B2 | 10/2006 | Yager et al. |
| 7,156,806 B2 | 1/2007 | Dobrovolny et al. |
| 7,189,246 B2 | 3/2007 | Otsuka et al. |
| 7,996,110 B2 | 8/2011 | Lipow et al. |
| 8,182,469 B2 | 5/2012 | Anderson et al. |
| 8,551,115 B2 | 10/2013 | Steger et al. |
| 8,554,368 B2 | 10/2013 | Fielding et al. |
| 10,022,195 B2 | 7/2018 | Scholan et al. |
| 2006/0106493 A1 | 5/2006 | Niemeyer et al. |
| 2006/0241414 A1* | 10/2006 | Nowlin .................. A61B 34/37 600/431 |
| 2007/0005002 A1 | 1/2007 | Millman et al. |
| 2007/0016174 A1 | 1/2007 | Millman et al. |
| 2007/0073493 A1 | 3/2007 | Ognier et al. |
| 2007/0083098 A1* | 4/2007 | Stern .................. A61B 1/00193 600/407 |
| 2007/0129634 A1 | 6/2007 | Hickey et al. |
| 2007/0137371 A1 | 6/2007 | Devengenzo et al. |
| 2009/0036740 A1 | 2/2009 | Finlay et al. |
| 2010/0160928 A1 | 6/2010 | Navas et al. |
| 2011/0071347 A1 | 3/2011 | Rogers et al. |
| 2011/0071541 A1 | 3/2011 | Prisco et al. |
| 2011/0277580 A1 | 11/2011 | Cooper et al. |
| 2013/0204271 A1 | 8/2013 | Brisson et al. |
| 2014/0309659 A1 | 10/2014 | Roh et al. |
| 2017/0086931 A1 | 3/2017 | Auld et al. |
| 2017/0086932 A1 | 3/2017 | Auld et al. |

FOREIGN PATENT DOCUMENTS

| | | |
|---|---|---|
| EP | 1125557 A2 | 8/2001 |
| JP | S6311291 A | 1/1988 |
| JP | 2015023884 A | 5/2015 |
| WO | WO-2006040466 A1 | 4/2006 |
| WO | WO-2007146987 A2 | 12/2007 |
| WO | WO-2010102119 A1 | 9/2010 |
| WO | WO-2011002215 A2 | 1/2011 |
| WO | WO-2011037718 A1 | 3/2011 |
| WO | WO-2015154172 A1 | 10/2015 |

OTHER PUBLICATIONS

Coopersurgical: RUMI II Brochure—Advanced Uterine Manipulation System, Delivering Superior Control and Enhanced Visualization, Dec. 2011, 8 pages.
Endoboy Pneumatic Manipulator Arm Instruction Manual, Dec. 7, 2002, Geyser S.A., France, pp. 1-21.
International Search Report and Written Opinion for Application No. PCT/US2017/042204, dated Nov. 28, 2017, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

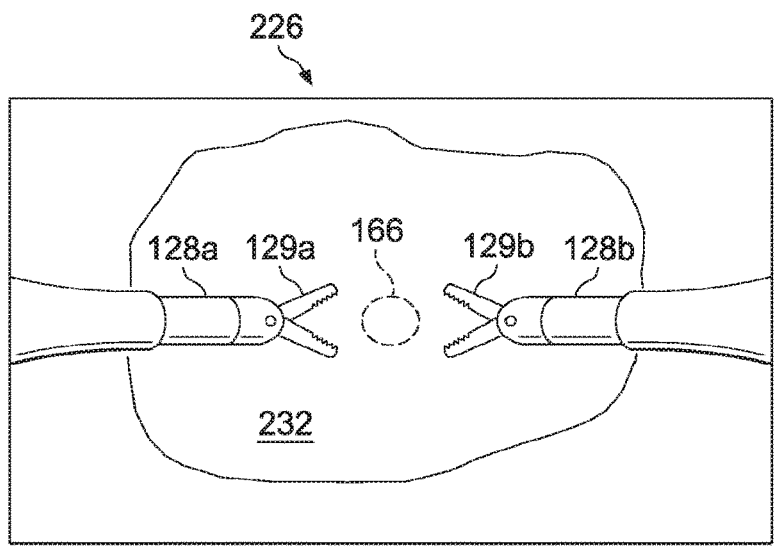
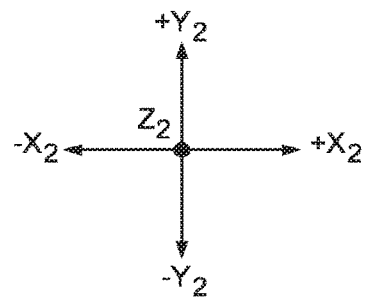
Fig. 14
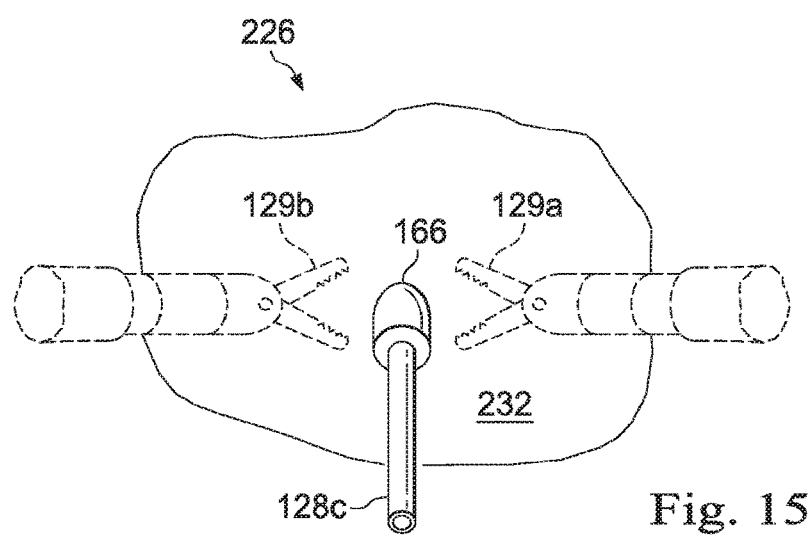
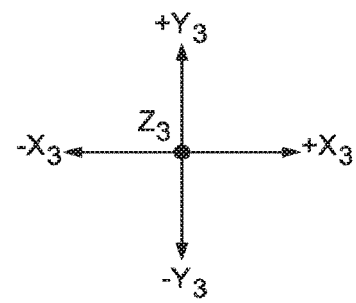
Fig. 15

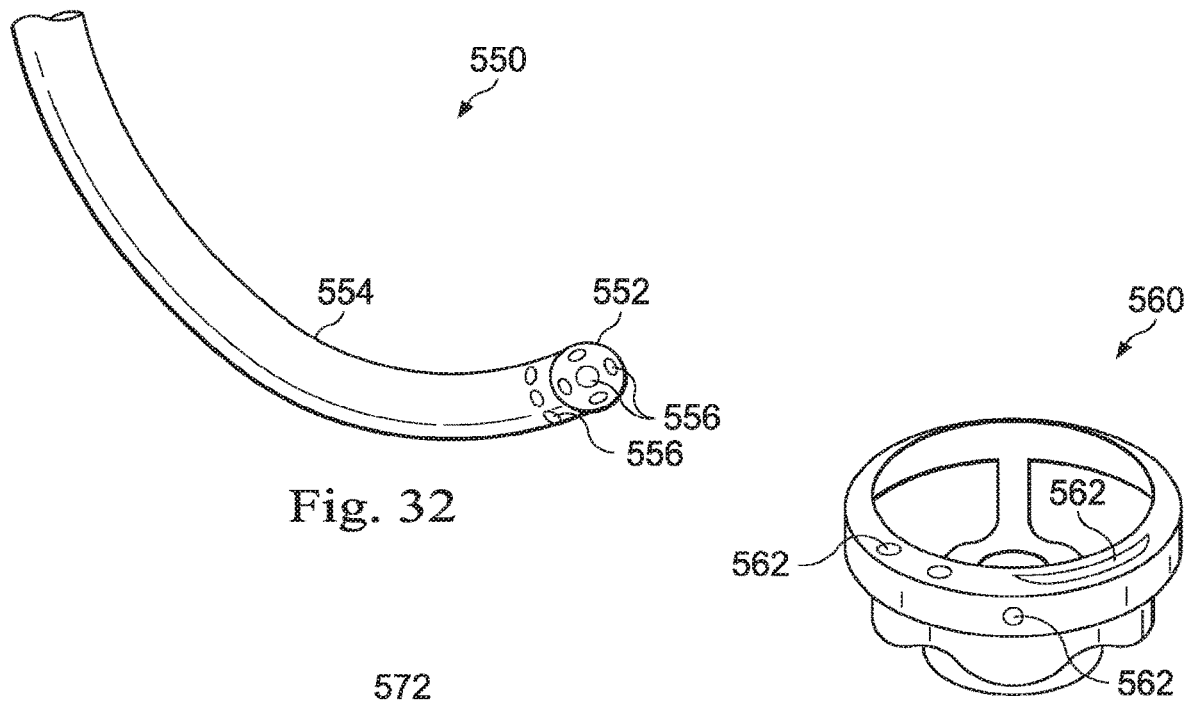
Fig. 32
Fig. 33
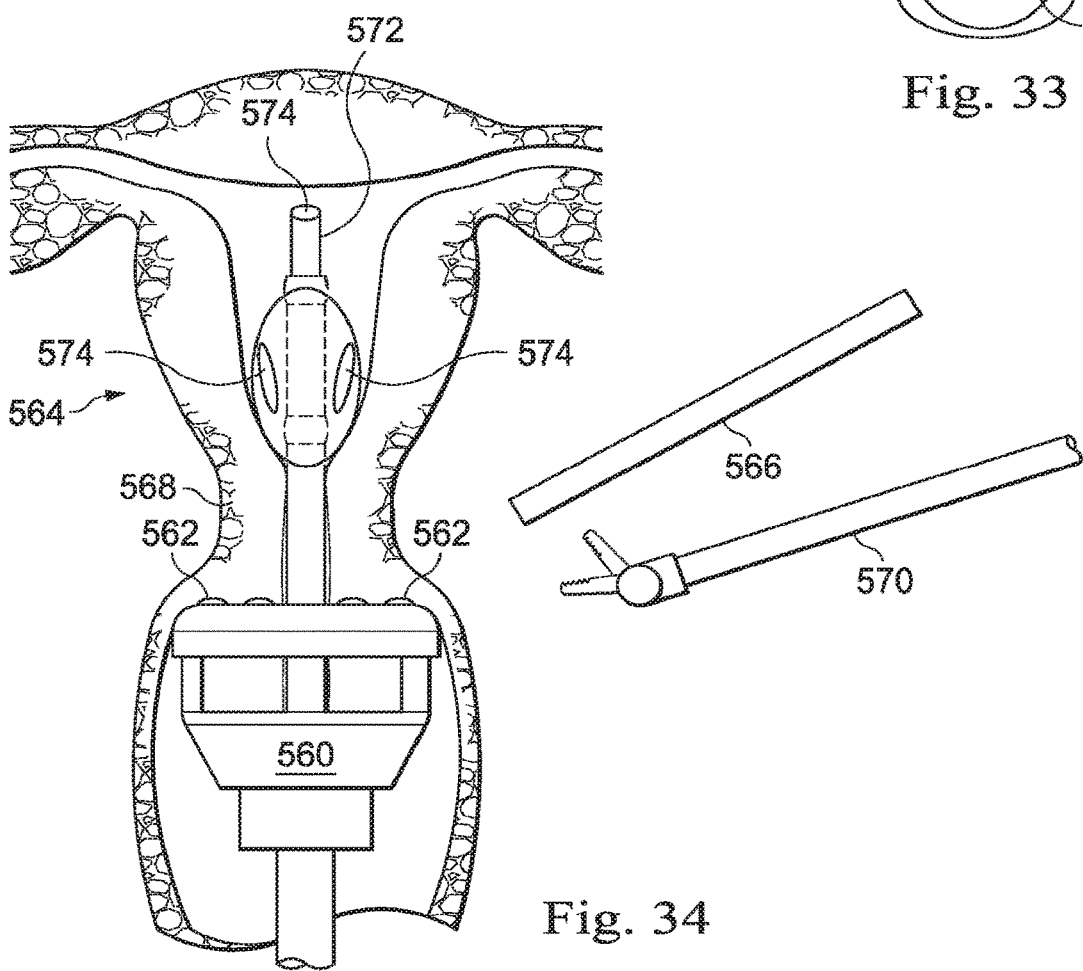
Fig. 34

SYSTEMS AND METHODS FOR CONTROLLING A SURGICAL INSTRUMENT

RELATED APPLICATIONS

This patent application is the U.S. national phase of International Application No. PCT/US2017/042204, filed Jul. 14, 2017, which designated the U.S. and claims priority to and the benefit of the filing date of U.S. Provisional Patent Application 62/362,406, entitled "SYSTEMS AND METHODS FOR CONTROLLING A SURGICAL INSTRUMENT," filed Jul. 14, 2016, all of which are incorporated by reference herein in their entirety.

FIELD

The present disclosure is directed to robotic systems and methods of use, including surgical systems and methods for use in minimally invasive teleoperational surgery, and including systems and methods for controlling an instrument for uterine manipulation.

BACKGROUND

Minimally invasive medical techniques are intended to reduce the amount of extraneous tissue that is damaged during diagnostic or surgical procedures, thereby reducing patient recovery time, discomfort, and harmful side effects. Minimally invasive telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted telesurgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side "slave" surgical manipulator. The configuration and motion of the master controls the instrument's position, orientation, and articulation at the surgical site via the patient side "slave" surgical manipulator. The slave is an electro-mechanical assembly which includes a plurality of arms, joints, linkages, servo motors, etc. that are connected together to support and control the surgical instruments. In a surgical procedure, the surgical instruments (including an endoscope) may be introduced directly into an open surgical site or more typically through cannulas into a body cavity.

For minimally invasive surgical procedures, the surgical instruments, controlled by the surgical manipulator, may be introduced into the body cavity through a single surgical incision site or through multiple closely spaced incision sites on the patient's body. For some minimally invasive surgical procedures, surgical instruments, particularly surgical assist tools such as probes, tissue manipulators, and retractors, may also be introduced into the surgical workspace through more remotely located surgical incisions or natural orifices. Improved systems and methods are needed for mounting and controlling these surgical instruments.

The instruments, systems, and methods described herein may be used for non-medical purposes including industrial uses, general robotic uses, manipulation of non-tissue work pieces, and/or cosmetic improvements. Other non-surgical applications include use on tissue removed from human or animal anatomies (without return to a human or animal anatomy) or on human or animal cadavers.

SUMMARY

The embodiments of the invention are summarized by the claims that follow below.

In one embodiment, a teleoperational medical system comprises an input device and a manipulator configured to couple with and move an instrument. The system also comprises a control system including one or more processors. In response to a determination that the instrument is inserted into an instrument workspace in a corresponding direction to a field of view of the workspace, the control system is configured to map movement of the input device to movement of the instrument according to a first mapping. In response to a determination that the instrument is inserted into the instrument workspace in a non-corresponding direction to the field of view, the control system is configured to map movement of the input device to movement of the instrument according to a second mapping. The second mapping includes an inversion of the first mapping for at least one direction of motion of the instrument.

In another embodiment, a method comprises generating master control signals based on a movement of a master controller in a master workspace and determining a direction of a field of view of an imaging device in an instrument workspace. The method also comprises determining whether a slave instrument direction for a slave instrument in the instrument workspace is corresponding to the direction of the field of view or is non-corresponding to the direction of the field of view. In response to a determination that the slave instrument direction is corresponding to the direction of the field of view, the method comprises mapping the movement of the master controller to movement of the slave instrument according to a first mapping and generating slave instrument control signals for movement of the slave instrument in the instrument workspace based on the first mapping. In response to a determination that the slave instrument direction is non-corresponding to the direction of the field of view, the method comprises mapping the movement of the master controller to movement of the slave instrument according to a second mapping and generating slave instrument control signals for movement of the slave instrument in the instrument workspace based on the second mapping. The second mapping includes an inversion of the first mapping for at least one direction of motion of the slave instrument.

In another embodiment, a teleoperational instrument system comprises a master input device in a master workspace, an actuated instrument end effector in an instrument workspace, and an actuated tissue probe in the instrument workspace. A method of operating the teleoperational instrument system comprises generating a set of master control signals in response to movement of the master input device and responsive to the set of master control signals, generating a first mapping. The first mapping maps the movement of the master input device to movement of the instrument end effector in the instrument workspace. Responsive to the set of master control signals, the method also comprises generating a second mapping. The second mapping maps the movement of the master input device to movement of the actuated tissue probe in the instrument workspace. In response to a determination that the master input device has control of the actuated instrument end effector, the method also includes generating a set of instrument control signals using the first mapping. In response to a determination that the master input device has control of the actuated tissue probe, the method comprises generating a set of instrument control signals using the second mapping. The second mapping includes an inversion of the first mapping for at least one direction of motion of the actuated tissue probe.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 10:
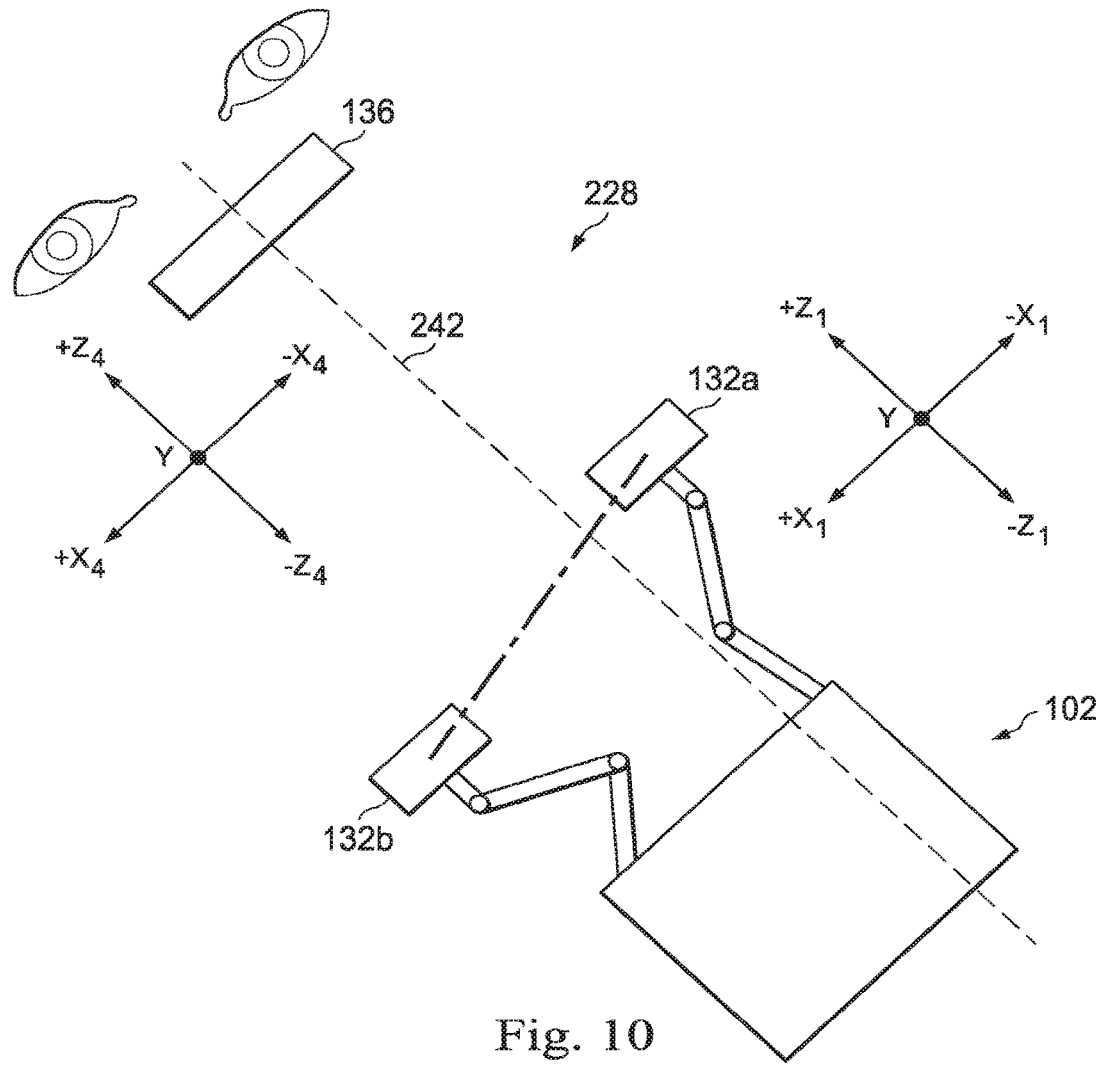

FIG. 10 is a schematic view of a surgeon's control console relative to a controller's three dimensional Cartesian coordinate reference system in a controller's workspace. The Cartesian coordinate reference frame shown in the figure has the Y-axis extending normal to and away from the plane of the page and is indicated with a solid dot in the center of the reference frame symbol. This labeling convention is used for all subsequent figures.

Figure 11:
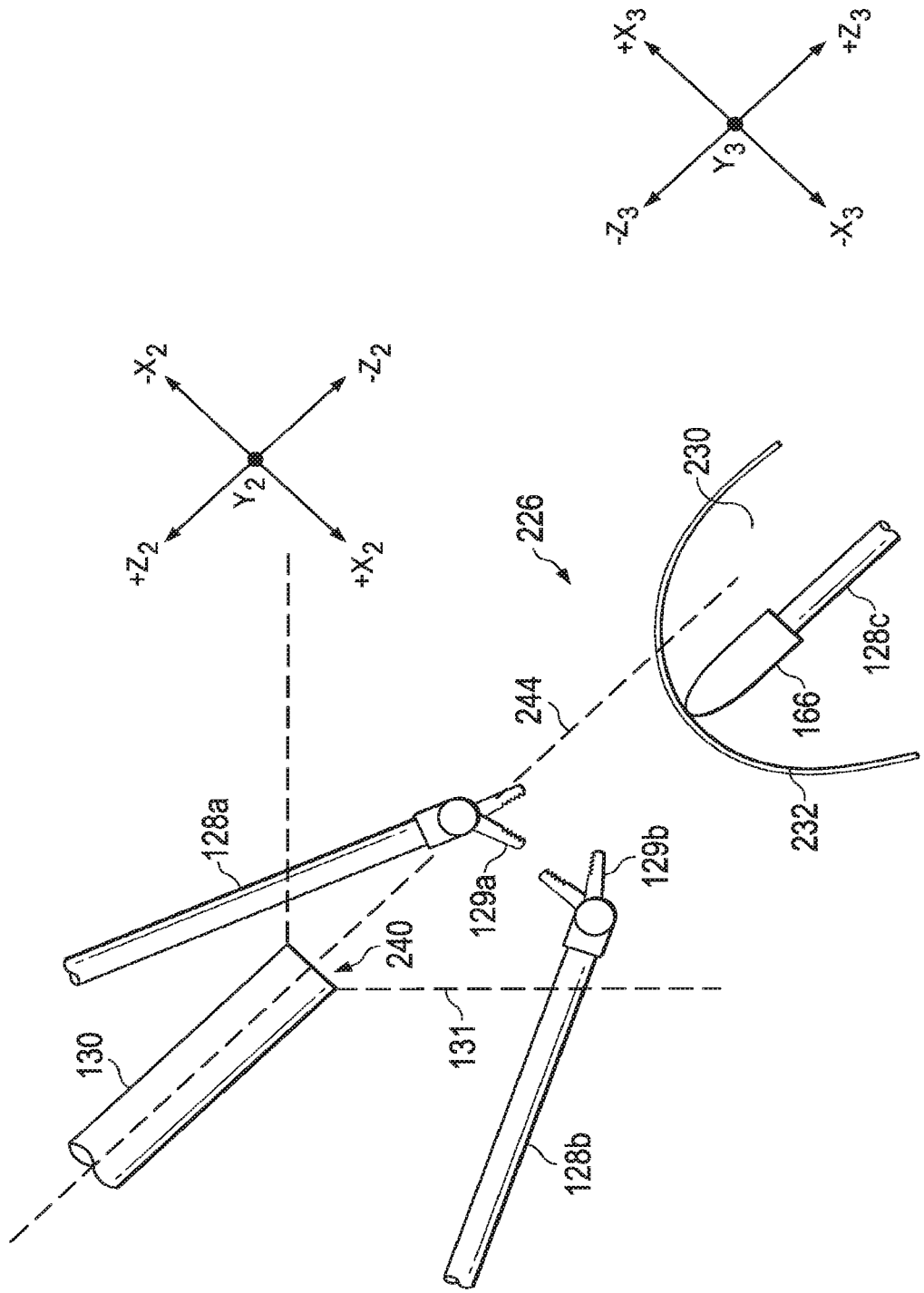

FIG. 11 is a schematic view of surgical instruments (including an endoscope) relative to a surgical three dimensional Cartesian coordinate reference system in an instrument workspace.

Figure 12:
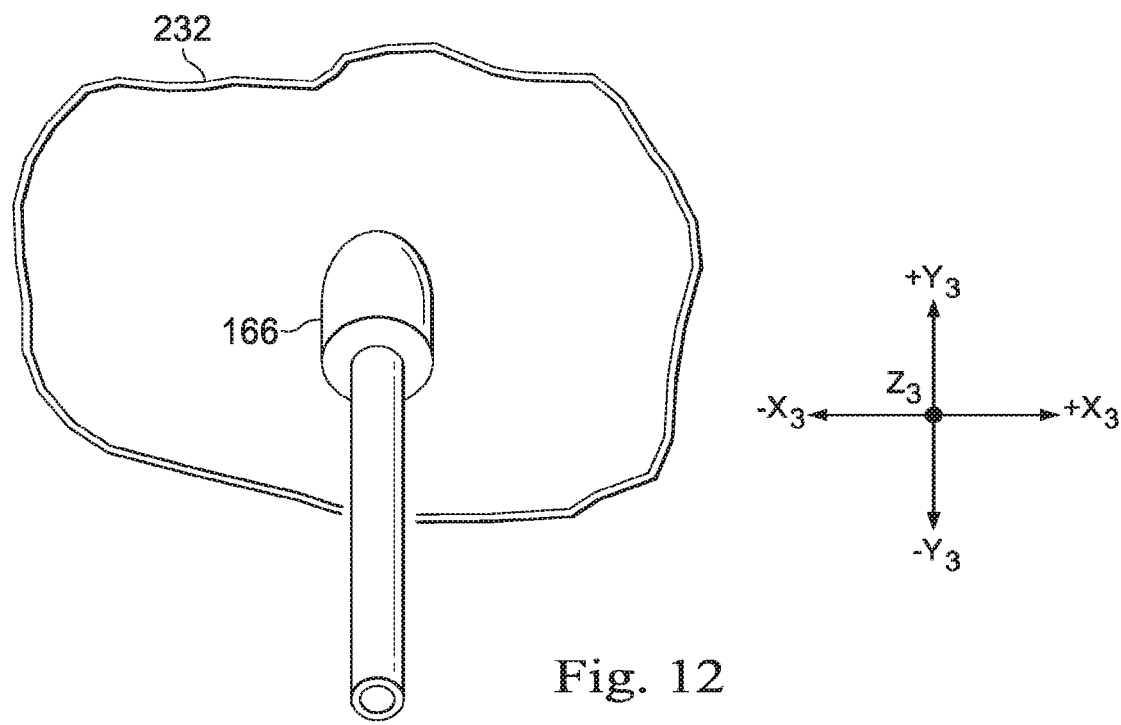

FIG. 12 is a view of an elevator instrument positioned within a body cavity.

Figure 13:
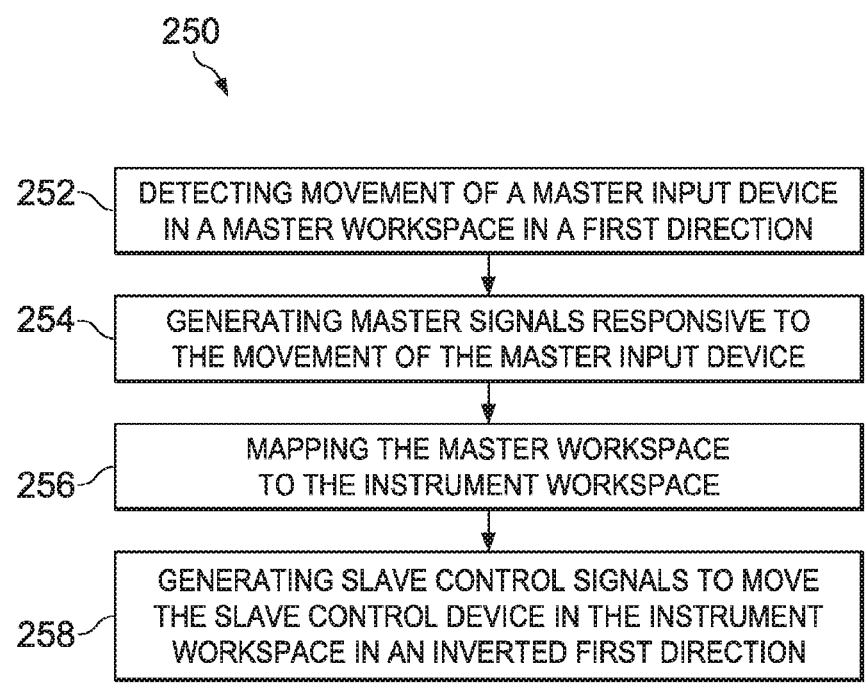

FIG. 13 is a process for controlling a surgical instrument, such an elevator instrument, using an inverted mapping technique.

FIG. 14 is an endoscopic user view of an instrument workspace with a uterine elevator instrument (shown with phantom lines to indicate that it is obscured from view) in a first position relative to a section of tissue. In this view, the uterine elevator instrument is behind tissue and is not directly visible via the endoscope.

FIG. 15 is a view of the instrument workspace of FIG. 14 with the uterine elevator instrument in the first position, from the probe frame.

Figure 16:
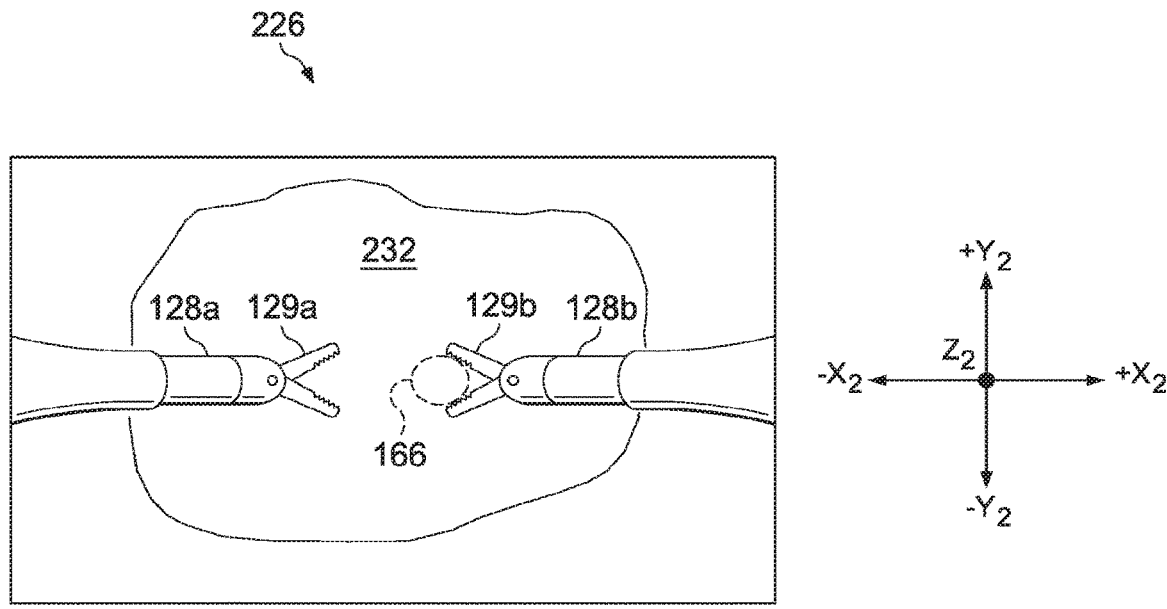

FIG. 16 is an endoscopic user view of the instrument workspace with the uterine elevator instrument (shown with phantom lines) in a second position relative to the section of tissue.

Figure 17:
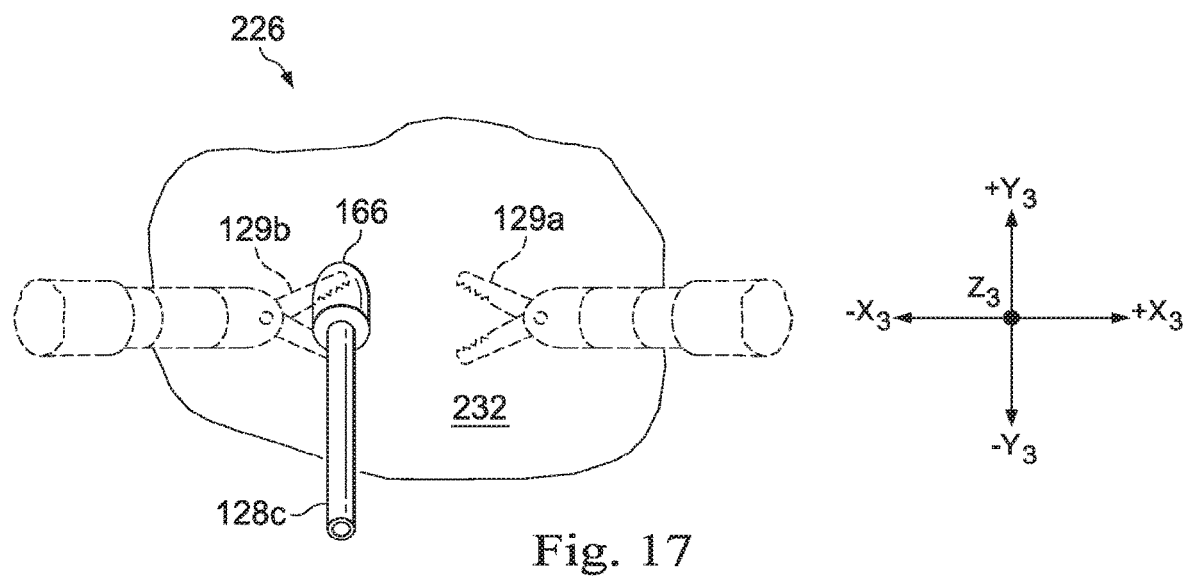

FIG. 17 is a view of the instrument workspace of FIG. 16 with the uterine elevator instrument in the second position, from the probe frame.

Figure 18:
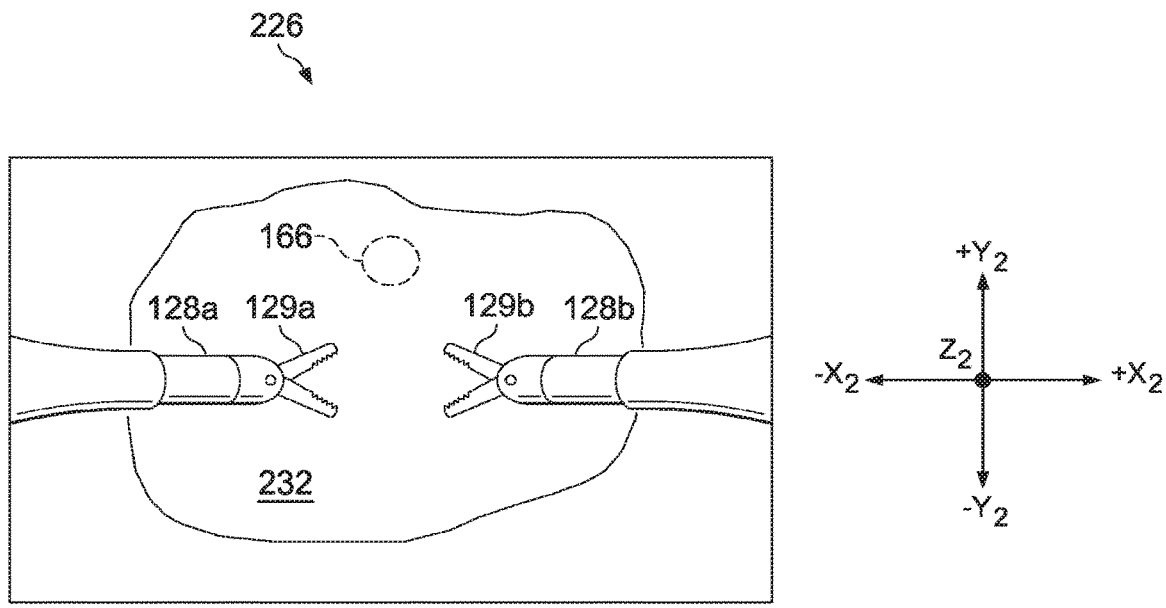

FIG. 18 is an endoscopic user view of the instrument workspace with the uterine elevator instrument (shown with phantom lines) in a third position relative to the section of tissue.

Figure 19:
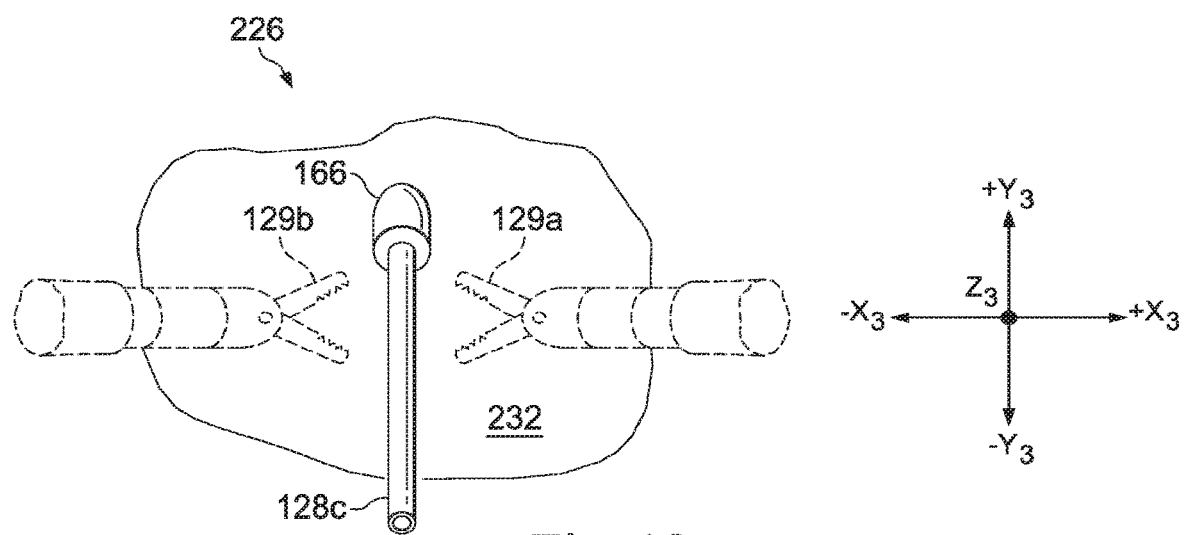

FIG. 19 is a view of the instrument workspace of FIG. 18 with the uterine elevator instrument in the third position, from the probe frame.

Figure 20:
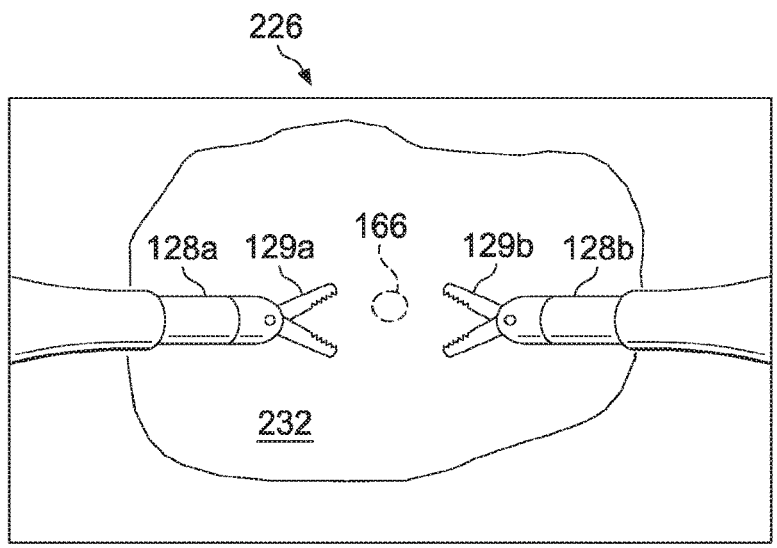

FIG. 20 is an endoscopic user view of the instrument workspace with the uterine elevator instrument (shown with phantom lines) in a fourth position relative to the section of tissue.

Figure 21:
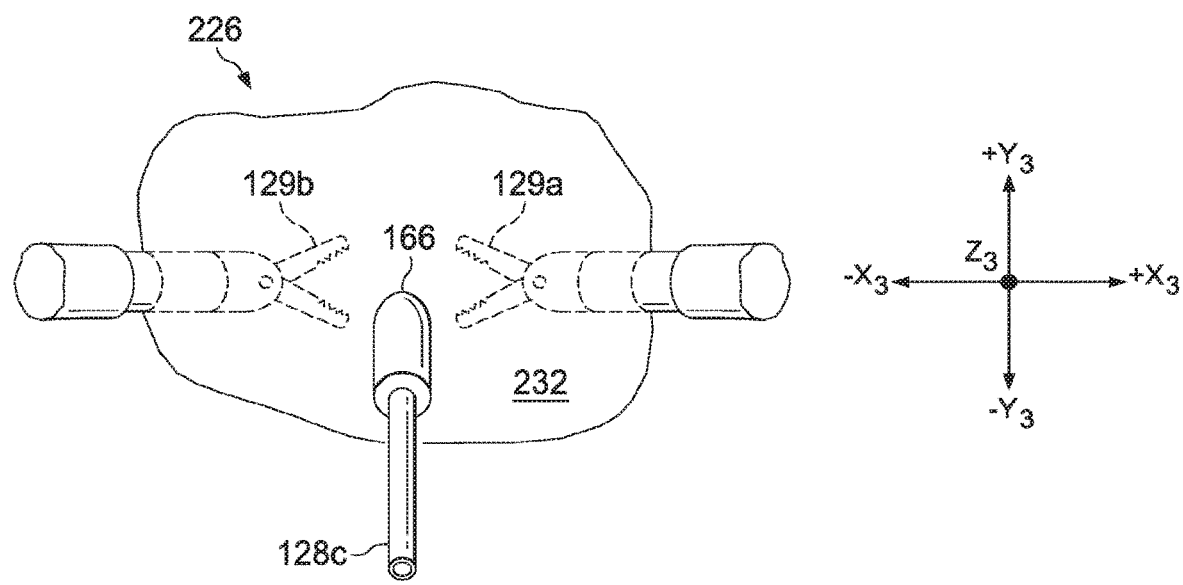

FIG. 21 is a view of the instrument workspace of FIG. 20 with the uterine elevator instrument in the fourth position, from the probe frame.

Figure 22:
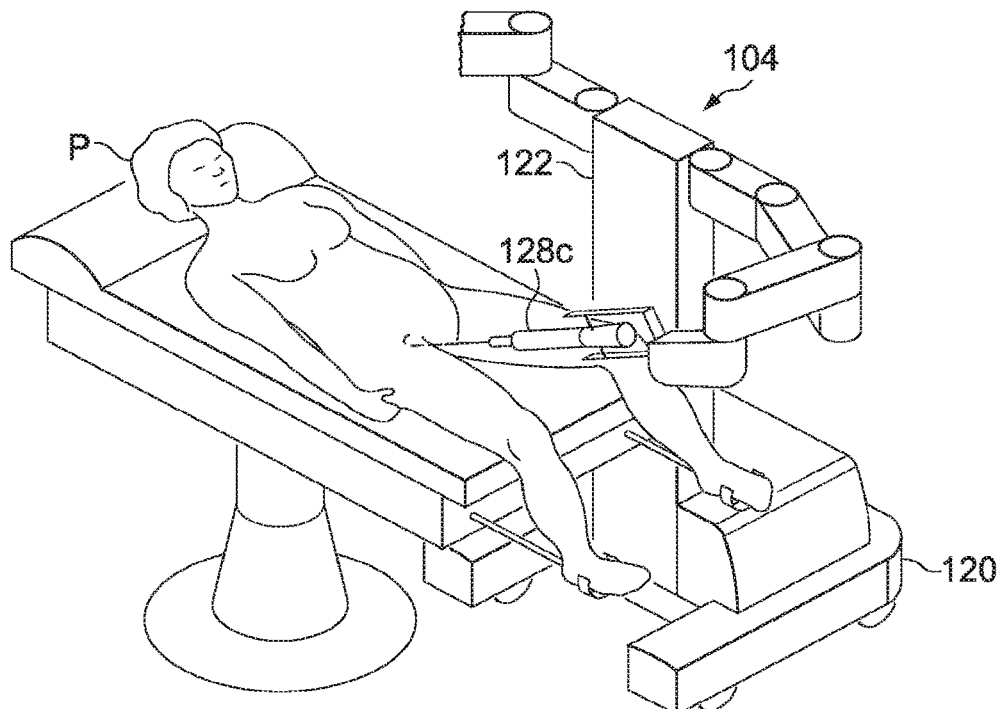

FIG. 22 is a schematic view of a free-standing slave manipulator with a mounted uterine elevator instrument.

Figure 23:
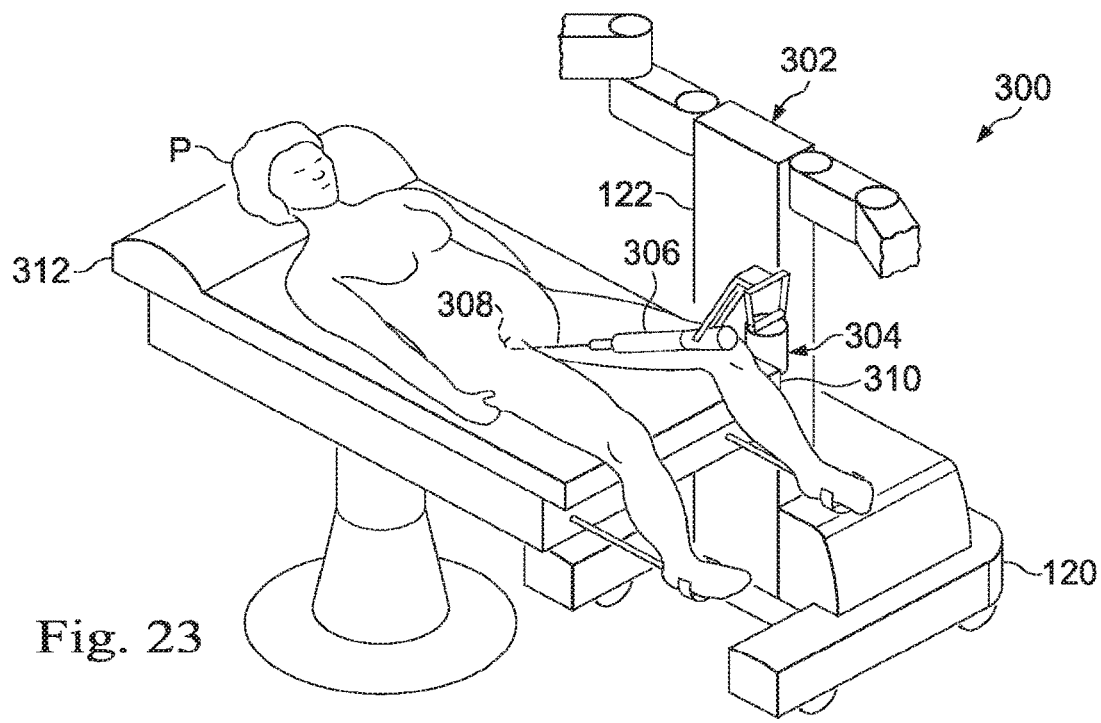

FIG. 23 is a schematic view of a bed-mounted slave manipulator with a mounted uterine elevator instrument.

Figure 24:
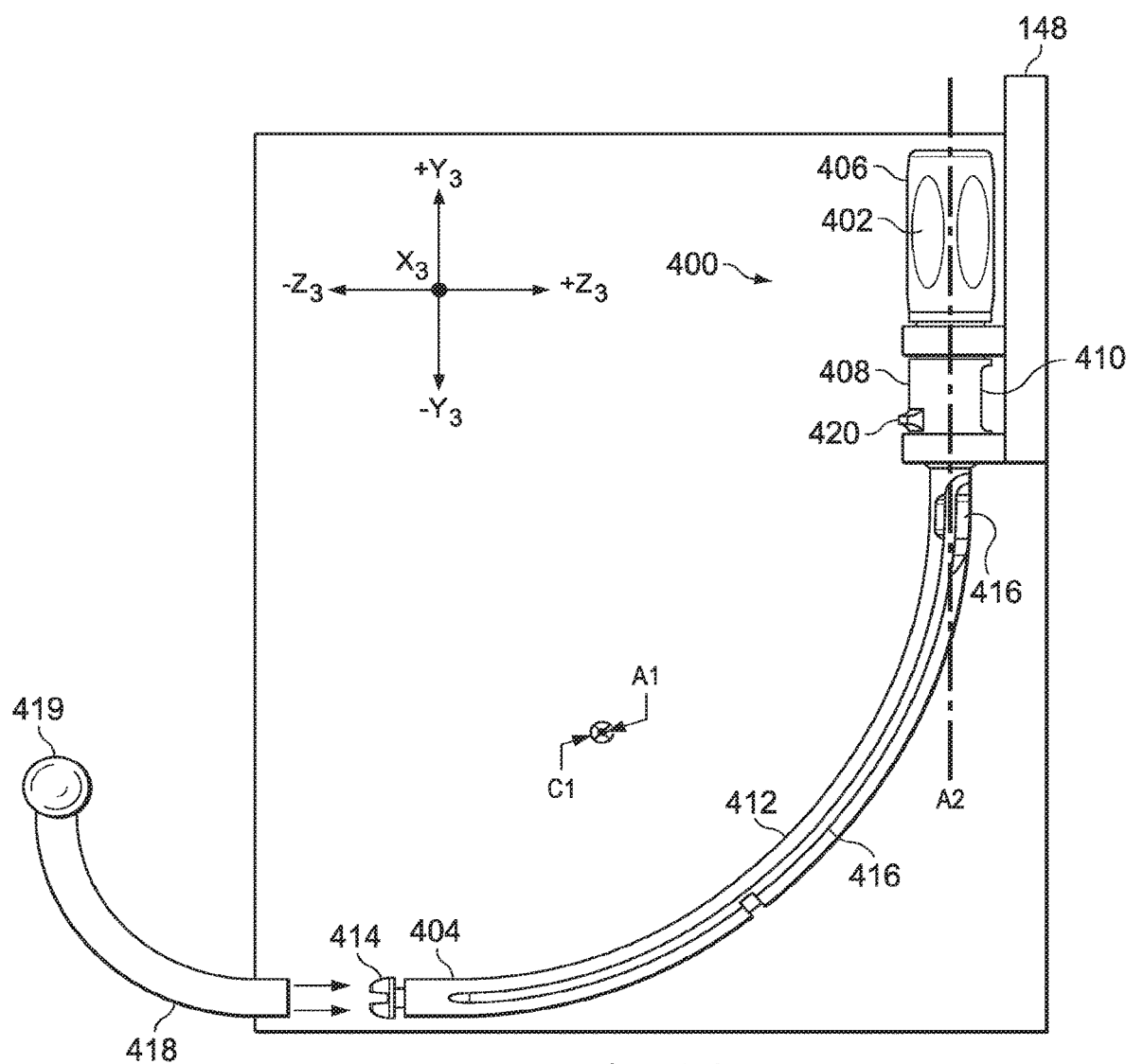

FIG. 24 is a side view of an assisting medical instrument according to an embodiment of the disclosure.

Figure 25:
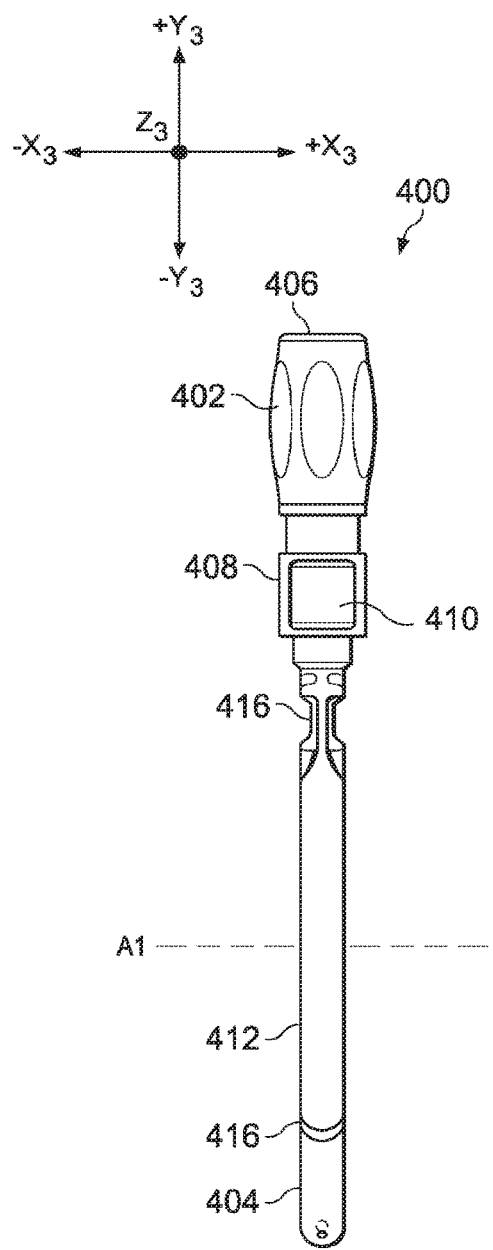

FIG. 25 is a rear view of the assisting medical instrument of FIG. 24.

Figure 26:
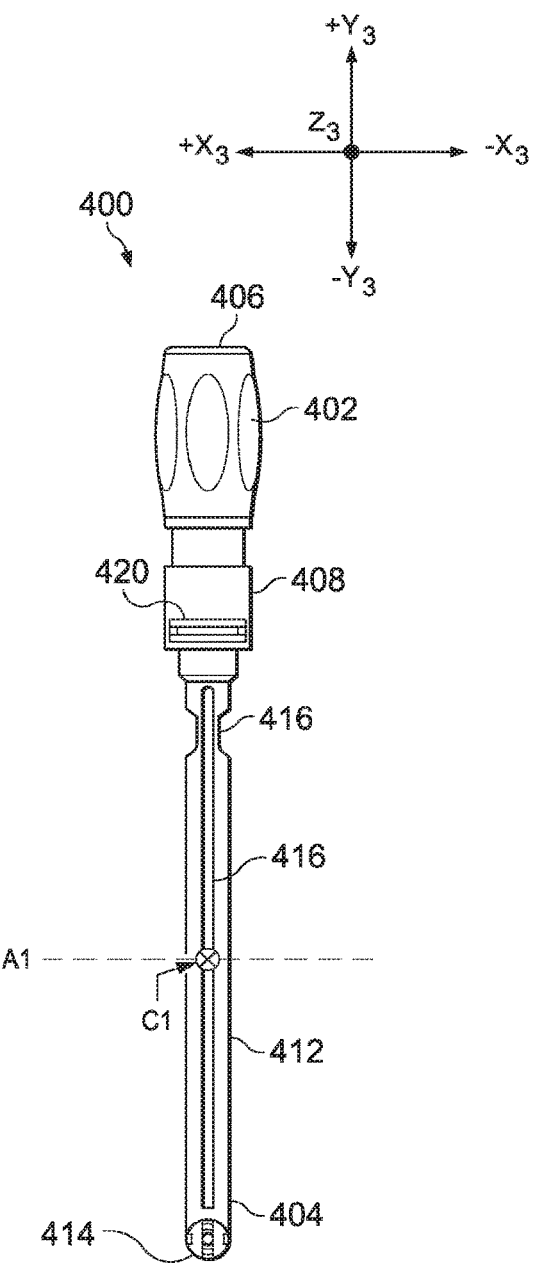

FIG. 26 is a front view of the assisting medical instrument of FIG. 24.

Figure 27:
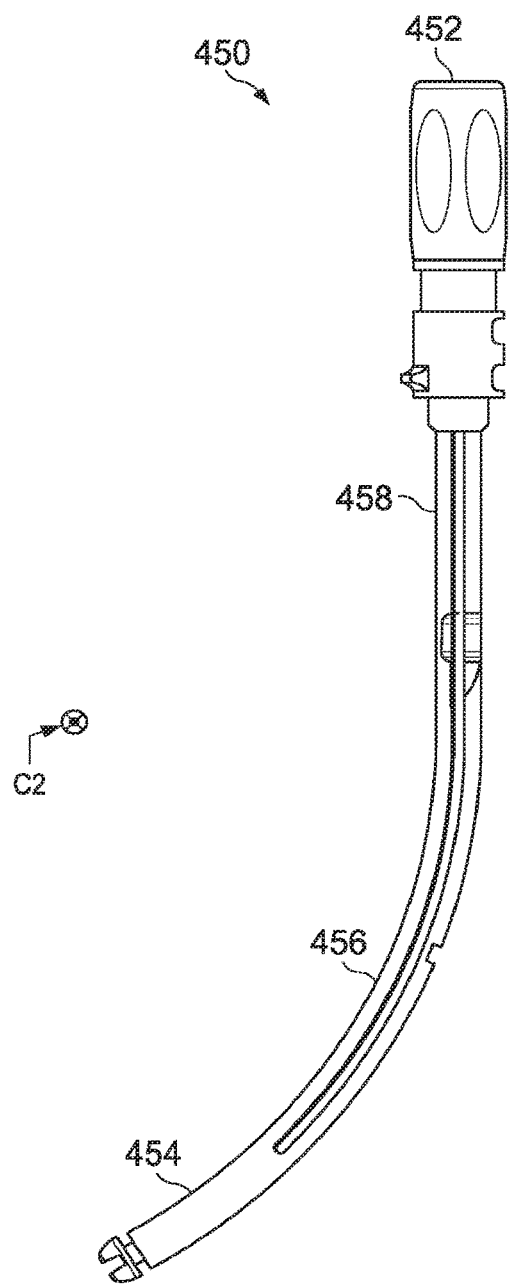

FIG. 27 is a side view of an assisting medical instrument according to another embodiment of the disclosure.

Figure 28:
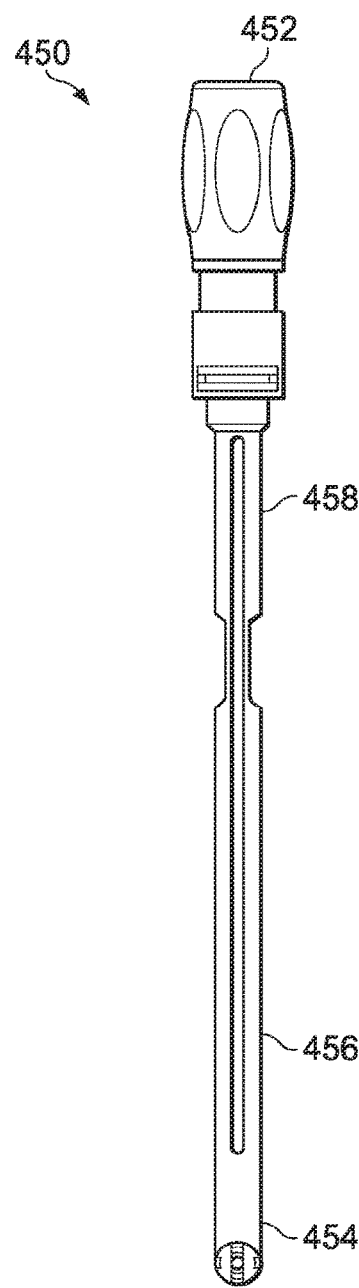

FIG. 28 is a front view of the assisting medical instrument of FIG. 27.

Figure 29:
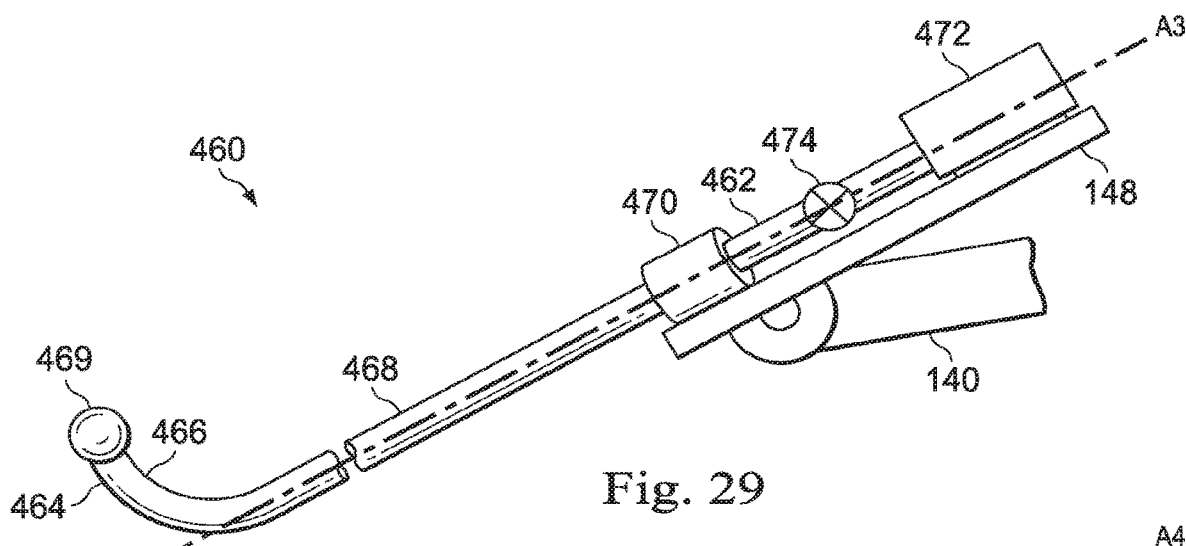

FIG. 29 is a schematic view of an assisting medical instrument with a joint assembly and a force transmission assembly according to one embodiment of the disclosure.

Figure 30:
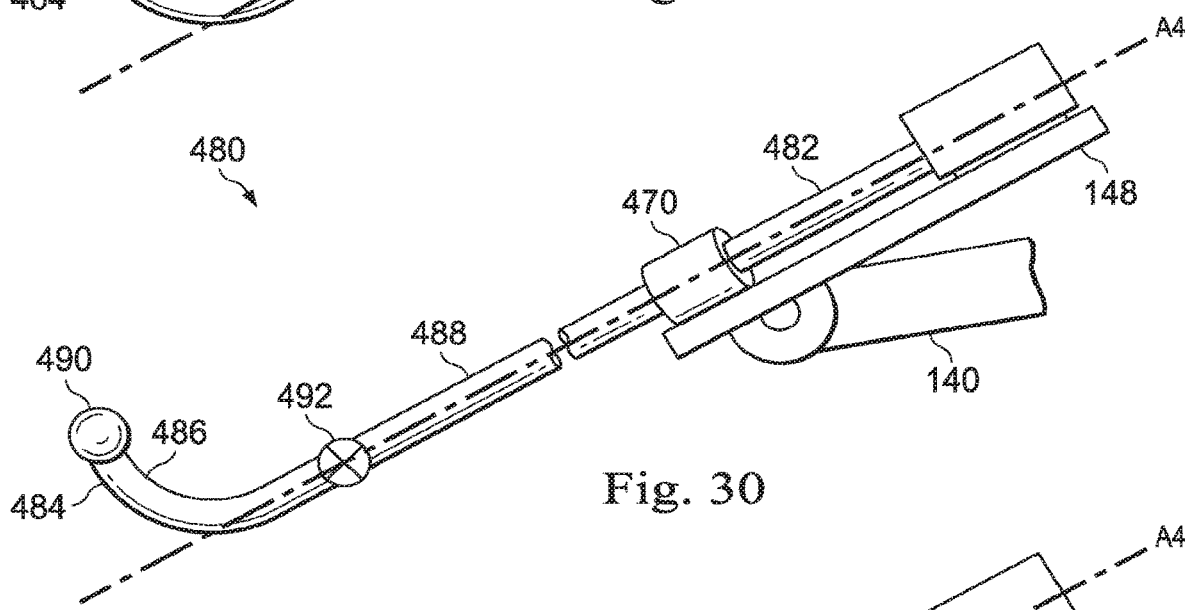

FIG. 30 is a schematic view of an assisting medical instrument with a joint assembly, and a force transmission assembly according to another embodiment of the disclosure.

Figure 31:
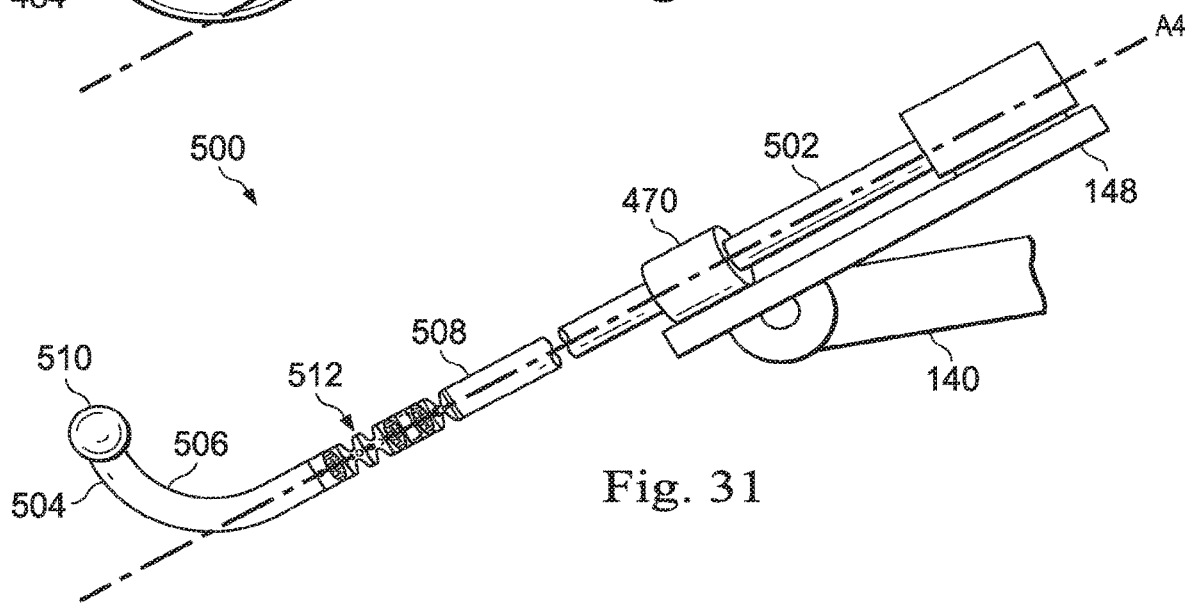

FIG. 31 is a schematic view of an assisting medical instrument with a joint assembly, and a force transmission assembly according to still another embodiment of the disclosure.

FIG. 32 illustrates an assisting medical instrument including a passive illumination source.

FIG. 33 illustrates a colpotomizer cup including a passive illumination source.

FIG. 34 illustrates the colpotomizer cup of FIG. 33 in use in a medical procedure.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Figure 1:
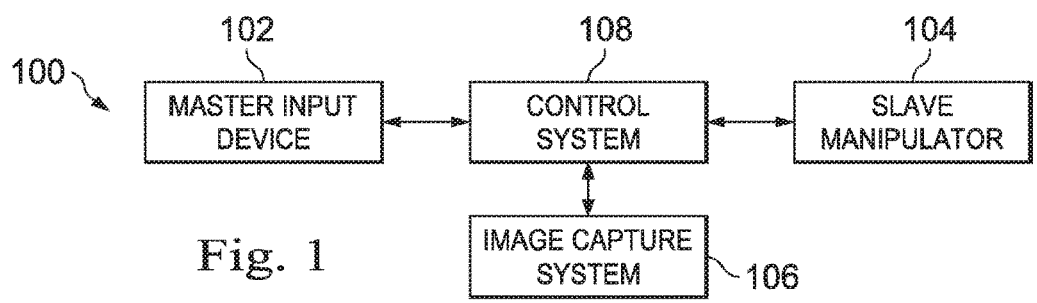
FIG. 1 is a schematic depiction of a teleoperational system according to an embodiment of the present disclosure.

Referring to FIG. 1 of the drawings, a teleoperational system is generally indicated by the reference numeral 100. The teleoperational surgical system 100 includes a master console 102, also referred to as a master or surgeon's console, for inputting a surgical procedure and a slave manipulator 104, also referred to as a patient-side manipulator (PSM), for the teleoperational movement of surgical instruments at a surgical site within a patient. The teleoperational surgical system 100 is used to perform minimally invasive teleoperational surgery. One example of a teleoperational surgical system that can be used to implement the systems and techniques described in this disclosure is a da Vinci® Surgical System manufactured by Intuitive Surgical, Inc. of Sunnyvale, Calif. In one embodiment the slave manipulator may be free-standing (see, FIG. 2). In an alternative embodiment, the slave manipulator may be mounted to other equipment in the surgical arena, including, for example, the surgical bed (see, FIG. 23). In still another alternative embodiment, the slave manipulator may include both free-standing and bed-mounted components.

The teleoperational surgical system 100 also includes an image capture system 106 which includes an image capture device, such as an endoscope, and related image processing hardware and software. The teleoperational surgical system 100 also includes a control system 108 that is operatively linked to sensors, motors, actuators, components of the master console 102, components of the slave manipulator 104 and to the image capture system 106.

The system 100 is used by a system operator, generally a surgeon, who performs a minimally invasive surgical procedure on a patient. The system operator sees images, captured by the image capture system 106, presented for viewing at the master console 102. In response to the surgeon's input commands, the control system 108 effects servomechanical movement of surgical instruments coupled to the teleoperational slave manipulator 104.

The control system 108 includes at least one processor and typically a plurality of processors for effecting control between the master manipulator 102, the slave manipulator 104, and the image capture system 106. The control system 108 also includes software programming instructions to implement some or all of the methods described herein. While control system 108 is shown as a single block in the simplified schematic of FIG. 1, the system may comprise a number of data processing circuits (e.g., on the surgeon's console 102 and/or on the slave manipulator system 104), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the teleoperational systems described herein. In one embodiment, control system 108 may support wireless communication protocols such as Bluetooth, IrDA, HomeRF, IEEE 802.11, DECT, and Wireless Telemetry.

Figure 2:
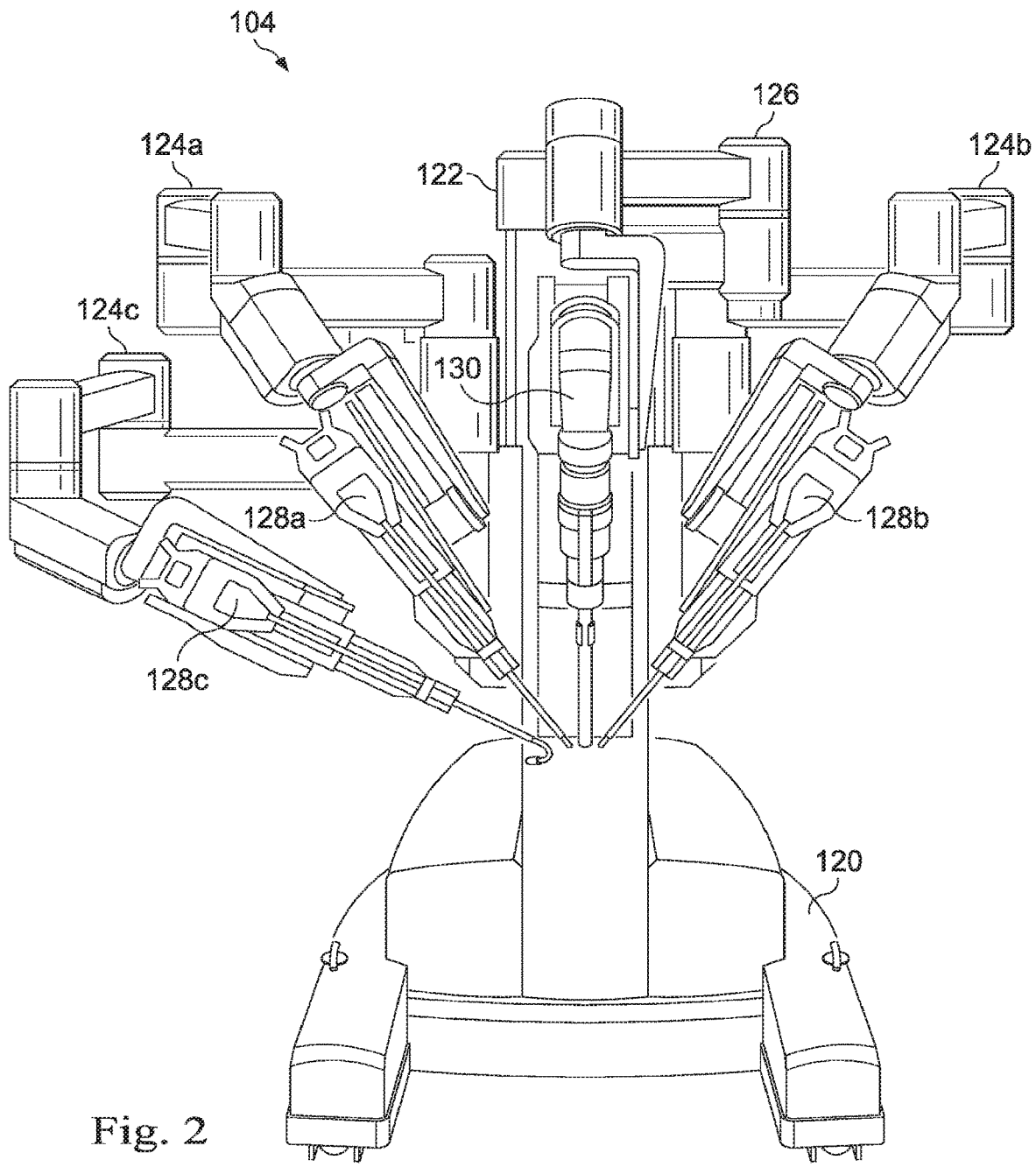
FIG. 2 is a front elevation view of a patient side cart including three patient side manipulators and one endoscopic manipulator according to one embodiment of the disclosure.

FIG. 2 is a front elevation view of the patient-side manipulator 104 according to one embodiment of the teleoperational surgical system 100. The patient-side manipulator 104 includes a base 120 that rests on the floor, a support tower 122 that is mounted on the base 120, and several arms that support surgical tools (including portions of the image capture system 106). As shown in FIG. 2, arms 124a, 124b are instrument arms that support and move the surgical instruments used to manipulate tissue, and arm 126 is a camera arm that supports and moves the endoscope. FIG. 2 also shows an optional third instrument arm 124c that is supported on the back side of support tower 122 and that can be positioned to either the left or right side of the patient-side manipulator as necessary to conduct a surgical procedure. FIG. 2 further shows interchangeable surgical instruments 128a, 128b, 128c mounted on the instrument arms 124a, 124b, 124c, respectively, and it shows endoscope 130 mounted on the camera arm 126. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm). The surgical instruments 128a, 128b include end effectors 129a, 129b, respectively. (See FIG. 11)

Figure 3:
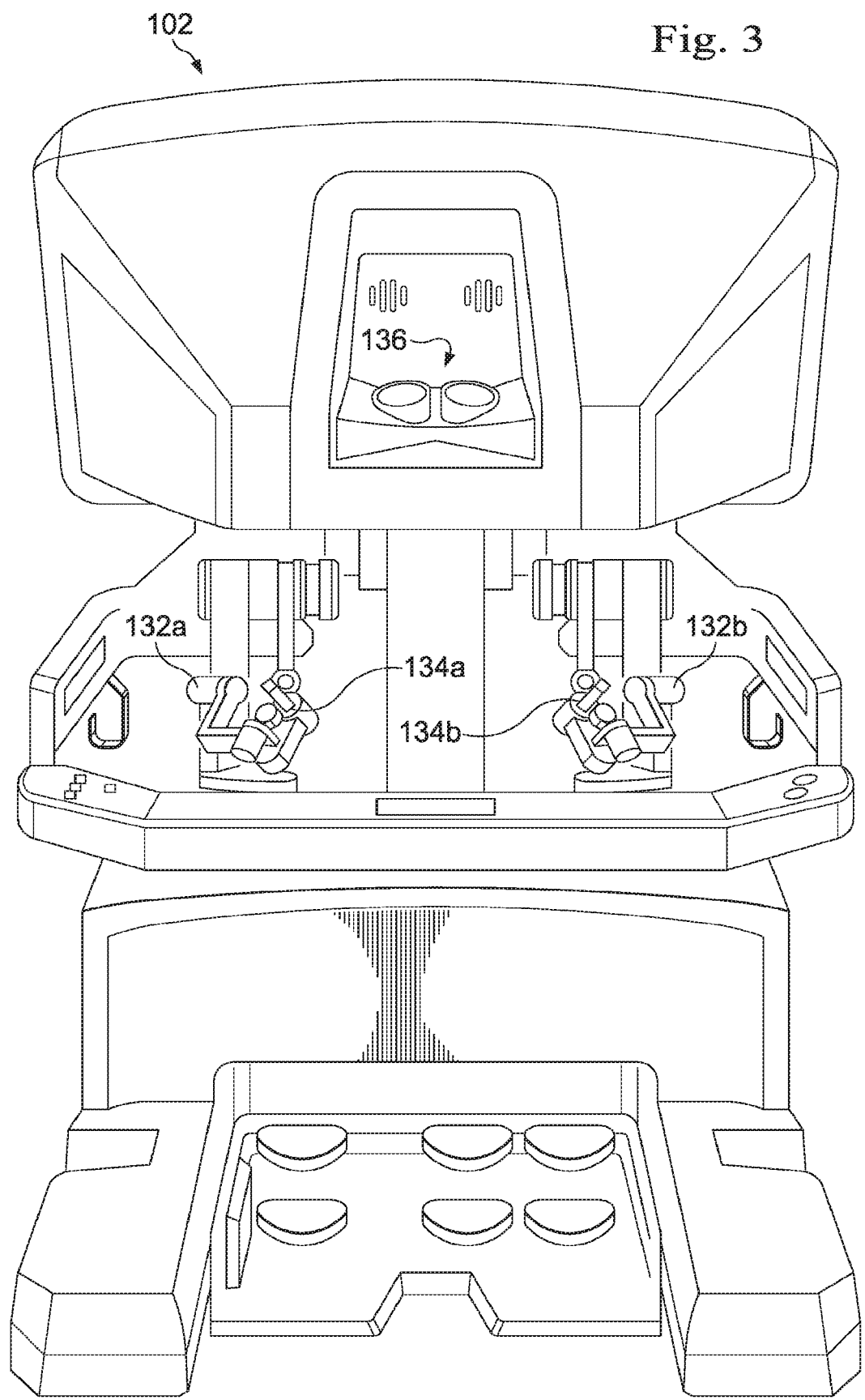
FIG. 3 is a front elevation view of a surgeon's console in a teleoperational surgical system according to one embodiment of the disclosure.

FIG. 3 is a front elevation view of a master console 102 component according to one embodiment of the teleoperational surgical system 100. The master console 102 is equipped with left and right multiple DOF master tool manipulators (MTM's) 132a, 132b, which are kinematic chains that are used to control the surgical tools (which include the endoscope and various cannulas). The MTM's 132 may be referred to simply as "master," and their associated arms 124 and surgical instruments 128 may be referred to simply as "slave." The surgeon grasps a pincher assembly 134a, 134b on each MTM 132, typically with the thumb and forefinger, and can move the pincher assembly to various positions and orientations. Each MTM 132a, 132b will generally allow movement within the master workspace with a plurality of degrees of freedom, typically with six degrees of freedom, three rotational degrees of freedom and three translational degrees of freedom.

When a tool control mode is selected, each MTM 132 is coupled to control a corresponding instrument arm 124 for the patient-side manipulator 104. For example, left MTM 132a may be coupled to control instrument arm 124a and instrument 128a, and right MTM 132b may be coupled to control instrument arm 124b and instrument 128b. If the third instrument arm 124c is used during a surgical procedure and is positioned on the left side, then left MTM 132a can be switched between controlling arm 124a and instrument 128a to controlling arm 124c and instrument 128c. Likewise, if the third instrument arm 124c is used during a surgical procedure and is positioned on the right side, then right MTM 132a can be switched between controlling arm 124b and instrument 128b to controlling arm 124c and instrument 128c. In alternative embodiments, the third instrument arm may be controlled by either the left or right MTM to accommodate surgical convenience. In some instances, control assignments between MTM's 132a, 132b and arm 124a/instrument 128a combination and arm 124b/ instrument 128b combination may also be exchanged. This may be done, for example, if the endoscope is rolled 180 degrees, so that the instrument moving in the endoscope's field of view appears to be on the same side as the MTM the surgeon is moving.

Surgeon's console 102 also includes a stereoscopic image display system 136. Left side and right side images captured by the stereoscopic endoscope 130 are output on corresponding left and right displays, which the surgeon perceives as a three-dimensional image on display system 136. In one configuration, the MTM's 132 are positioned below display system 136 so that the images of the surgical tools shown in the display appear to be co-located with the surgeon's hands below the display. This feature allows the surgeon to intuitively control the various surgical tools in the three-dimensional display as if watching the hands directly. Accordingly, the MTM servo control of the associated instrument arm and instrument is based on the endoscopic image reference frame.

The endoscopic image reference frame (i.e., "the image frame" or the "first instrument frame") is also used if the MTM's are switched to a camera control mode. For example, if the camera control mode is selected, the surgeon may move the distal end of the endoscope by moving one or both of the MTM's together (portions of the two MTM's may be servomechanically coupled so that the two MTM portions appear to move together as a unit). The surgeon may then intuitively move (e.g., pan, tilt, zoom) the displayed stereoscopic image by moving the MTM's as if holding the image in the hands.

The surgeon's console 102 is typically located in the same operating room as the patient-side manipulator 104, although it is positioned so that the surgeon operating the console is outside the sterile field. One or more assistants typically assist the surgeon by working within the sterile surgical field (e.g., to change tools on the patient side cart, to perform manual retraction, etc.). Accordingly, the surgeon operates remote from the sterile field, and so the console may be located in a separate room or building from the operating room. In some implementations, two consoles 102 (either co-located or remote from one another) may be networked together so that two surgeons can simultaneously view and control tools at the surgical site.

FIG. 22 illustrates the slave manipulator 104 with a patient P positioned for surgery. In this embodiment, the slave manipulator 104 is free-standing and the surgical instruments and the uterine elevator are all mounted to the free-standing base 120 and support tower 122. For clarity, some of the instrument arms and instruments have been omitted.

Figure 4:
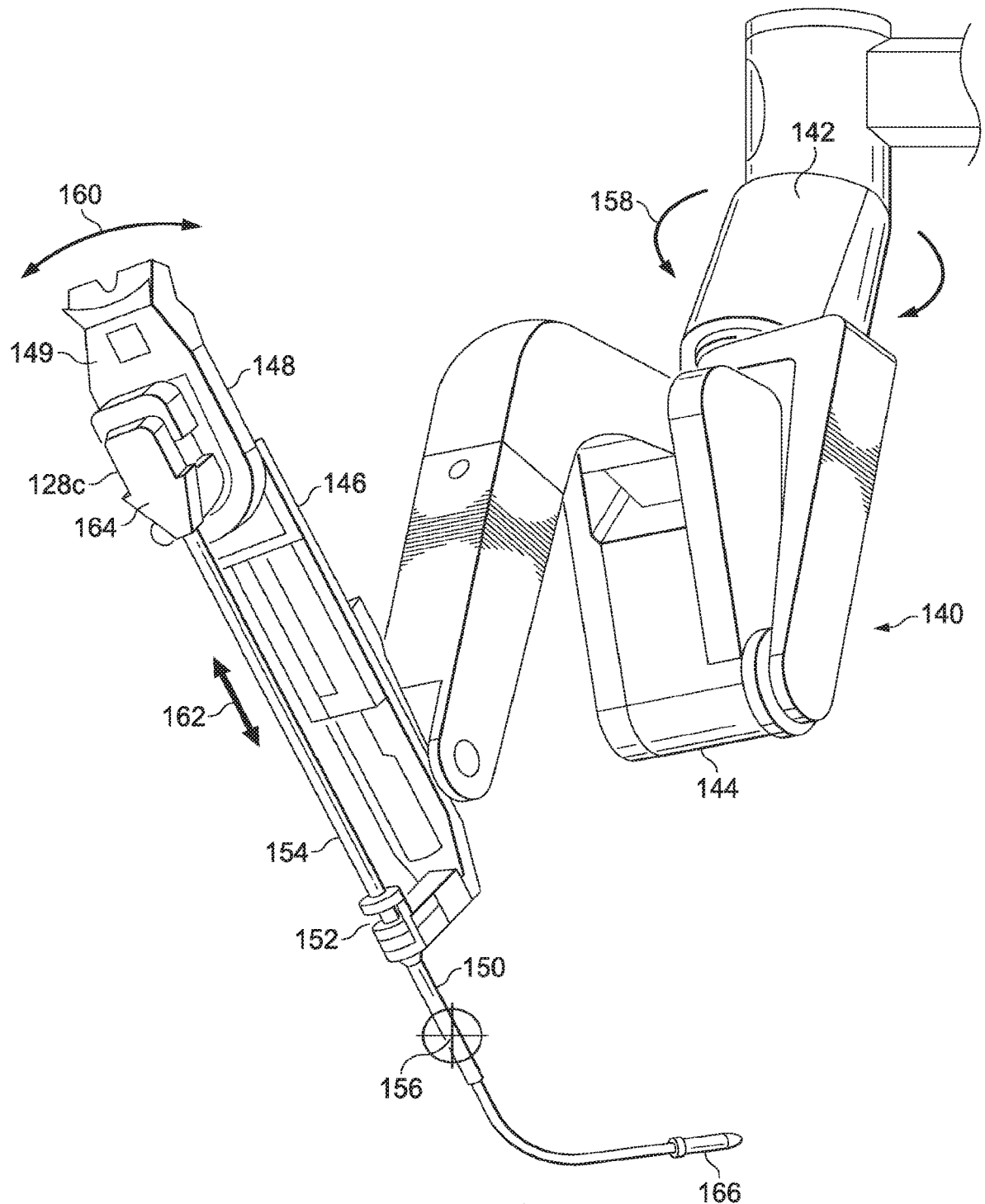
FIG. 4 is a perspective view of a patient side manipulator arm with a mounted surgical instrument according to one embodiment of the disclosure.

FIG. 4 is a perspective view of a portion of the control arm 124c with the mounted surgical instrument 128c. Sterile drapes and associated mechanisms that are normally used during surgery are omitted for clarity. The manipulator 140 includes a yaw servo actuator 142, a pitch servo actuator 144, and an insertion and withdrawal ("I/O") actuator 146. The surgical instrument 128c is shown mounted at an instrument spar 148 including a mounting carriage 149. An illustrative straight cannula 150 is shown mounted to cannula mount 152. Shaft 154 of instrument 128c extends through cannula 150. Manipulator 140 is mechanically constrained so that it moves instrument 128c around a stationary remote center of motion 156 (also called "remote center 156") located along the instrument shaft. Yaw actuator 142 provides yaw motion 158 around remote center 156, pitch actuator 144 provides pitch motion 160 around remote center 156, and I/O actuator 146 provides insertion and withdrawal motion 162 through remote center 156. Typically the remote center of motion 156 is locked at the incision in the patient's body wall during surgery and to allow for sufficient yaw and pitch motion to be available to carry out the intended surgical task. Alternatively, the remote center of motion may be located outside of the body to allow a greater range of motion without contacting the patient. Knowledgeable persons will understand that motion around a remote center of motion may be constrained by the use of software or by a physical constraint defined by a mechanical assembly.

Matching force transmission disks in mounting carriage 149 and instrument force transmission assembly 164 couple actuation forces from actuators in manipulator 140 to move various parts of instrument 128c in order to position and orient a tissue probe 166 mounted at the distal end of the curved shaft 154. Such actuation forces may typically roll instrument shaft 154 (thus providing another DOF through the remote center 156). Embodiments of force transmission assemblies are provided in U.S. Pat. No. 6,331,191 (filed Oct. 15, 1999; disclosing "Surgical Robotic Tools, Data Architecture, and Use") and U.S. Pat. No. 6,491,701 (filed Jan. 12, 2001; disclosing "Mechanical Actuator Interface System for Robotic Surgical Tools") which are incorporated herein by reference in its entirety. In alternative embodiments, the instrument 128c may include a wrist at the distal end of the shaft that provides additional yaw and pitch DOF's. The tissue probe 166 may be, for example, a general tissue manipulator, a tissue elevator, or a tissue retractor. In alternative embodiments, the instrument 128c may include an imaging component.

Figure 5:
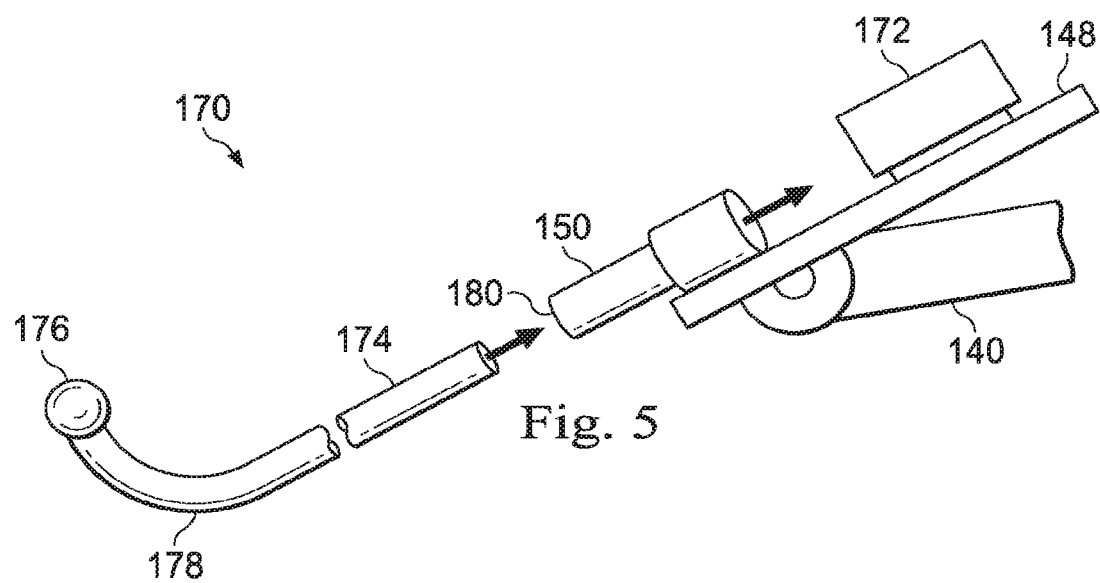
FIG. 5 is an exploded schematic view of a uterine elevator, cannula, and surgical manipulator according to one embodiment of the disclosure.

FIG. 5 depicts an exploded schematic view of a two-piece surgical instrument 170 that may be mounted to the manipulator 140 of FIG. 4. In this embodiment, the straight cannula 150 is mounted to the instrument spar 148. The instrument 170 includes a force transmission assembly 172, a shaft 174, and a tissue probe 176. In this embodiment, the shaft 174 is a rigid rod with a curved portion 178. In alternative embodiments, the shaft may be cannulated and/or flexible. The shaft 174 may be sterilizable and may include a back-loadable tissue probe or vaginal fornices delineator such as a KOH Cup produced by Cooper Surgical, Inc. of Trumbull, Conn. The tissue probe 176 may be integrated with the shaft or may be removable and disposable. The instrument 170 is assembled by loading the shaft 174 through a distal end 180 of the cannula 150 and into engagement with the force transmission assembly 172. With the described configuration, any instrument insertion or removal motion may be along the instrument axis associated with spar 148. The curved nature of the shaft allows the instrument the versatility to manipulate tissue that is difficult to reach with a straight instrument. In one embodiment, the tissue probe 176 may be a uterine elevator tip for intrauterine manipulation, but other instruments such as a vaginal fornices delineator, retractors, actuated instruments, non-actuated instruments, or imaging devices may also be used for uterine procedures or surgical procedures at other anatomical locations.

Figure 6:
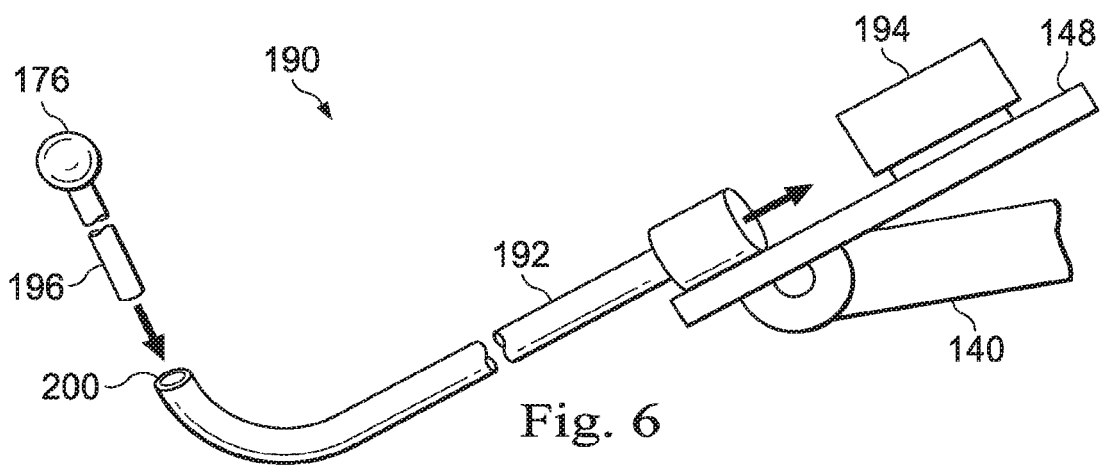
FIG. 6 is an exploded schematic view of a uterine elevator, cannula, and surgical manipulator according to a second embodiment of the disclosure.

FIG. 6 depicts an exploded schematic view of a two-piece surgical instrument 190 that may be mounted to the manipulator 140 of FIG. 4. In this embodiment, a curved cannula 192 is mounted to the instrument spar 148. The instrument 190 includes a force transmission assembly 194, a shaft 196, and a tissue probe 176. In this embodiment, the shaft 196 is a flexible rod. In one embodiment, the tissue probe 176 may be a uterine elevator tip for intrauterine manipulation, but other instruments such as vaginal fornices delineator, retractors, actuated instruments, non-actuated instruments, or imaging devices may also be used for uterine procedures or surgical procedures at other anatomical locations. The tissue probe 176 may be integrated with the shaft or may be removable and disposable. The instrument 190 is assembled by loading the shaft 196 through a distal end 200 of the curved cannula 192 and into engagement with the force transmission assembly 194. The flexible nature of the shaft allows it to bend for insertion through the curved cannula.

Figure 7:
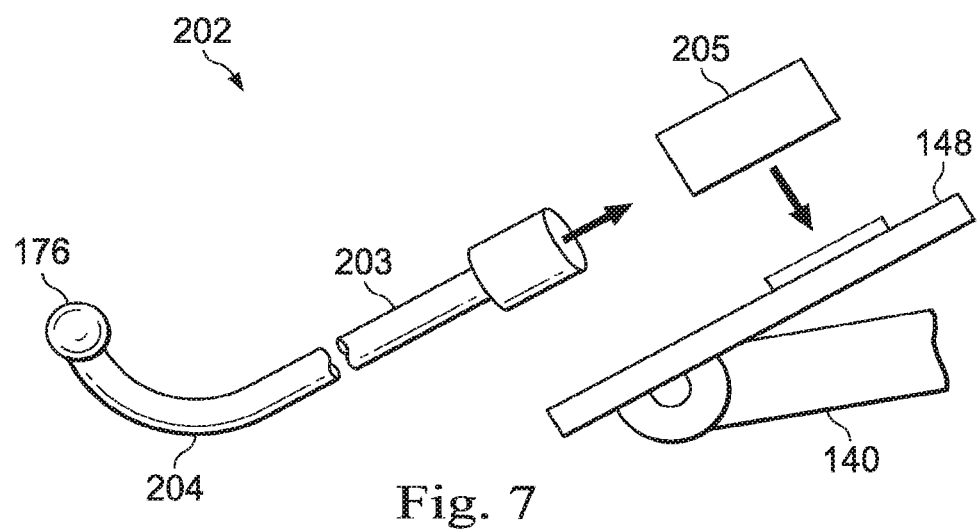
FIG. 7 is an exploded schematic view of a uterine elevator, cannula, and surgical manipulator according to a third embodiment of the disclosure.

FIG. 7 depicts a schematic view of a one-piece surgical instrument 202 that may be mounted to the manipulator 140 of FIG. 4. In this embodiment, the instrument 202 includes a tissue probe 176, a curved shaft segment 204, and straight shaft segment 203 that can be mounted directly to spar 148 instead of a cannula. In this embodiment, the shaft 203 is a rigid rod with a rigid curved segment 204. In one embodiment, the tissue probe 176 may be a uterine elevator tip for intrauterine manipulation, but other instruments such as a vaginal fornices delineator, retractors, actuated instruments, non-actuated instruments, or imaging devices may also be used for uterine procedures or surgical procedures at other anatomical locations. To accommodate actuated instruments, the shaft may be cannulated and/or non-rigid. The tissue probe 176 may be integrated with the shaft or may removable and disposable. Instead of the force transmission assembly 194 of FIG. 4, a "dummy" force transmission assembly 205 is shown attached to spar 148. The instrument 202 is assembled by attaching the shaft 203 directly to spar 148 in place of a cannula. The "dummy" force transmission assembly can be installed during operation to allow the system to recognize the type of instrument being attached via an electronic identification mechanism built into the force transmission 205 housing. The "dummy" force transmission assembly can thus signal that the tissue probe is ready for use in a following mode. Further description of a "dummy" or "mock" instrument is provided in U.S. Provisional Application 61/594,130 (filed Feb. 2, 2012; disclosing "Systems and Methods for Controlling a Robotic Surgical System"), which is incorporated by reference herein in its entirety. In another alternative, shaft 203 may include a stop feature to prevent random rotation relative to the spar 148. Alternatively, shaft 203 may have the capability of being rotationally indexed on the axis of the shaft. Alternatively, the force transmission assembly may include a marker for determining the rotational position of the shaft 203 to aid in calculating the tissue probe 176 location.

Figure 8:
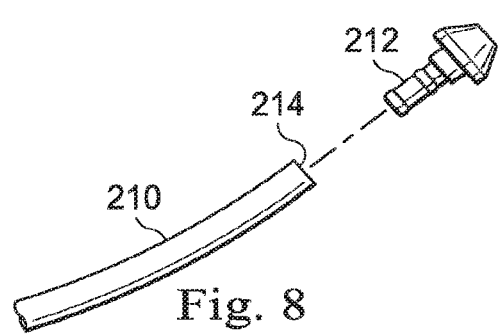
FIG. 8 is a side view of a tool fastener for use with a curved cannula.
Figure 9:
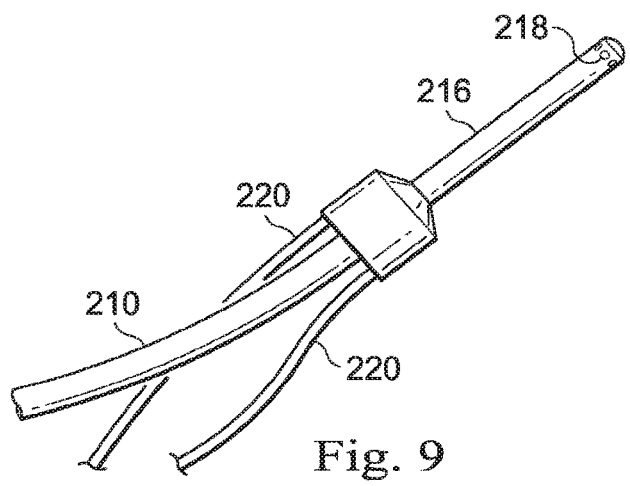
FIG. 9 is a side view of a uterine elevator for use with the tool fastener and curved cannula of FIG. 8.

Another embodiment of a surgical instrument is disclosed in FIGS. 8 and 9. In this embodiment, a tissue probe is attachable to a distal end of a cannulated shaft that is mountable to an I/O insertion spar as previously described. Specifically, FIG. 8 depicts a curved cannulated shaft 210 and a tip fastener 212 sized for insertion into a distal end 214 of the curved cannulated shaft. The tip fastener 212 may be mechanically coupled to the curved cannula 210 via, for example, a threaded coupling, a snap coupling, a friction coupling, or other known mechanical coupling. Suitable cannulated shafts may include, for example, 5 or 8 mm cannulated shafts. Larger or smaller cannulated shafts may also be suitable within the anatomical constraints of the patient. As shown in FIG. 9, a tissue probe 216 is mechanically coupled to the tip fastener 212. The tissue probe 216 includes distal openings 218 connected to tubing 220. The tubing 220 is used to irrigate and suction a surgical site via the tissue probe 216. In alternative embodiments where I/O motion is not required, tissue probes may be mounted directly to cannulas mounted to the insertion spar as (such as the cannulas shown in FIGS. 5 and 6*a*).

In the above described embodiments, the cannulas and the instrument shafts may be formed of rigid materials such as stainless steel or glass-epoxy composite. Alternatively, they may be formed of flexible materials such as a high modulus of elasticity plastic like Polyether ether ketone (PEEK), glass or carbon filled Polyether ether ketone (PEEK), or a glass-fiber-epoxy or a carbon-fiber-epoxy composite construction. The inside and outside diameters and physical construction of the shaft or cannula are chosen uniquely for each material choice to limit the magnitude of forces that can be applied to the body during use or allow the structure to bend sufficiently to follow a curved guide path within the instrument or cannula during use. Additional information about the cannulas and instrument shafts, including information about material composition and flexibility, is provided in detail in U.S. patent application Ser. No. 12/618,608 (filed Nov. 13, 2009; disclosing "Curved Cannula Instrument") which is incorporated herein by reference, in its entirety.

FIG. 10 schematically illustrates the master console 102. FIG. 11 schematically illustrates components (including instruments 130, 128*a*, 128*b*, 128*c*) of the slave manipulator 104. As shown in FIG. 10, the surgeon views an instrument workspace 226 through the viewer of the display system 136. The tissue probe 166 carried on the instrument spar 148 is caused to perform positional and orientational movements within the instrument workspace 226 in response to movement and action inputs on an associated master control in a master workspace 228 (also "master space 228"). As previously described, the instrument arm 124*c* may be controlled by either the MTM 132*a* or the MTM 132*b*. In this illustrative embodiment, the instrument arm 124*c* with the surgical instrument 128*c* including the tissue probe 166 will be controlled by the left MTM 132*a*. A different master frame of reference $(X_1, Y_1, Z_1)$ is associated with each one of the MTMs. It is understood that other frames of reference may be defined within the master workspace. For example, a viewer frame of reference $(X_4, Y_4, Z_4)$ may be associated with the viewer of display system 136. The relationships between the frames of reference in the master workspace may be established by fixed kinematic relationships, by sensors, or other known relationships.

As shown in FIG. 11, during the surgical set-up procedure, the surgical instrument 128*c* is positioned within a body cavity 230 and the tissue probe 166 is positioned against a tissue wall 232 of the body cavity 230. The body cavity may be any surgically created or naturally formed body cavity. In one embodiment, for example, the body cavity is the uterus of a patient and the instrument is inserted through the cervix, into the uterus, and into contact with the uterine wall. During gynecological procedures, the tissue probe, which may be a uterine elevator, serves to elevate and move the uterine tissue wall so that it will be properly positioned for access by the end effectors associated with the surgical instruments. FIG. 12 is a view of the tissue probe 166 positioned against the tissue wall 232 from within the body cavity 230. This view from a position at a proximal end of the tissue probe 166 will also be described as the "probe frame" or "second instrument frame" $(X_3, Y_3, Z_3)$ within the instrument workspace 226. The instrument frame may also be defined at other locations within the body cavity or at other locations along the shaft of the instrument 128*c*.

During a surgical procedure, images of the end effectors 129*a*, 129*b* and the surrounding instrument workspace are captured by the endoscope 130 having a field of view 131. These images from the viewpoint or field of view 131 of the endoscope are displayed on the display system 136 so that the surgeon sees the responsive movements and actions of the end effectors 129a, 129b as he or she controls such movements and actions by means of the MTM's 132a, 132b, respectively.

The field of view 131 captured by the endoscope 130 has an endoscopic frame of reference ($X_2$, $Y_2$, $Z_2$) within the instrument workspace 226. In this field of view, visualization of the tissue probe 166 is obstructed by the tissue wall 232. However, protrusion of the tissue wall 232 and movement of the protrusion due to movement of the tissue 166 on the opposite side of the tissue wall may be visualized in the field of view 131 of endoscope 130. The control system 108 is arranged to cause orientational and positional movement of the tissue probe 166, as viewed in the image at the viewer of the display system 136 to be mapped by orientational and positional movement of MTM 132a of the master manipulator 102 as will be described in greater detail below.

The probe frame, the endoscopic frame, frames of reference for each of the end effectors 129a, 129b, and any other frames of reference defined within the instrument workspace 226 may have known relationships established by fixed kinematic connections or by sensors.

In the description which follows, the control system will be described with reference to MTM 132a and instrument arm 124c with surgical instrument 128c. Control between master and slave movement is achieved by comparing master position and orientation in the master workspace 228 having a master Cartesian coordinate reference system with slave position and orientation in an instrument workspace 226 having a surgical Cartesian coordinate reference system. For ease of understanding and economy of words, the term "Cartesian coordinate reference system" will simply be referred to as "frame" in the rest of this specification. Accordingly, the control system 108 serves to compare the slave position and orientation within the endoscopic frame with the master position and orientation in the master frame (and/or viewer frame) and will actuate the slave to into a position and/or orientation in the endoscopic frame that corresponds with the position and/or orientation of the master in the master frame (and/or viewer frame). As an MTM is translated and rotated in three dimensional space, the master frame of reference translates and rotates correspondingly. These master frame translations and rotations may be sensed, and they may transformed (also "mapped") to the frames of reference in the instrument workspace, including the probe frame, to provide a control relationship between the MTM and coupled instruments and/or probe in the workspace by using well known kinematic calculations. As the master frame position and orientation is changed, the frame of the coupled instrument is changed correspondingly, so that the coupled instrument movement is slaved to the MTM movement.

As previously described, the control system 108 includes at least one, and typically a plurality, of processors which compute new corresponding positions and orientations of the slave in response to master movement input commands on a continual basis determined by the processing cycle rate of the control system.

As shown in FIG. 10, The $Z_1$-axis of the master frame through the master workspace moves with the MTM 132a. Naturally, the $X_1$ and $Y_1$-axes extend perpendicularly from the $Z_1$-axis. Also as shown in FIG. 10, the $Z_4$-axis of the viewer frame through the master workspace extends along (or parallel to) a line of sight of the surgeon, indicated by axis 242, when viewing the surgical site through the viewer of the display system 136. Naturally, the $X_4$ and $Y_4$-axes extend perpendicularly from the $Z_4$-axis. Conveniently, the $Y_4$ axis is chosen to extend generally vertically relative to the viewer of the display system 136 and the $X_4$ axis is chosen to extend generally horizontally relative to the viewer.

As shown in FIG. 11, the $Z_2$-axis of the endoscopic frame extends axially along (or parallel to) a viewing axis 244 of the endoscope 130. Although in FIG. 11, the viewing axis 244 is shown in coaxial alignment with a shaft axis of the endoscope 130, it is to be appreciated that the viewing axis can be angled relative thereto. Thus, the endoscope can be in the form of a straight or angled-tip scope. The $X_2$ and $Y_2$-axes are positioned in a plane perpendicular to the $Z_2$-axis. Also shown in FIG. 11, the $Z_3$-axis of a probe frame extends axially along (or parallel to) a longitudinal axis of the instrument 128c. The $X_3$ and $Y_3$-axes are positioned in a plane perpendicular to the $Z_3$-axis.

Additional information about a referenced control system, including information about the mapping of the position and orientation of the master in the master workspace with the instrument in the instrument workspace, is provided in detail in U.S. Pat. No. 6,424,885 B1 (filed Aug. 13, 1999; disclosing "Camera Referenced Control in a Minimally Invasive Surgical Apparatus") which is incorporated herein by reference, in its entirety. Generally, a surgical teleoperational mapping method includes moving a MTM in a master workspace by articulating a plurality of master joints. Master control signals, corresponding to the position, orientation, and velocity of the MTM are transmitted to the control system. In general, the control system will generate corresponding slave motor signals to map the Cartesian position of the master in the master workspace with the Cartesian position of the end effector or tissue probe in the instrument workspace according to a transformation. The control system may derive the transformation in response to state variable signals provided from the image capture system so that an image of the end effector or tissue probe in the display system appears substantially connected to the MTM. Additionally, position and velocity in the master workspace are transformed into position and velocity in the instrument workspace using scale and offset converters. Further details of the transformation are provided in U.S. Pat. No. 6,424,885 which was previously incorporated by reference herein. A surgical tissue probe or end effector is moved in the instrument workspace by articulating a plurality of slave joints in response to slave motor signals. The slave motor signals are generated by the control system in response to moving the master so that an image of the end effector or tissue probe in the display appears substantially connected with the MTM in the master workspace.

Because the surgeon has a distal end-on view of the tissue probe 166 through the display system 136, conventional mapping of the master to the slave would require the MTM 132a to be twisted to point back at the surgeon in an ergonomically awkward position and orientation. Therefore, a method of inverting the mapping of the master to the slave along at least one of the coordinates will allow the surgeon to control the tissue probe 166 as though the instrument 128c was extending from the tissue probe back toward the surgeon. In other words, as will be described in detail below, the movement of the MTM 132 is mapped to the tissue probe 166 in a reversed direction along at least one coordinate of the probe frame.

In a conventional mapping technique, movement of the MTM 132a in a +$X_4$ direction results in a corresponding movement (including scaling and offset factors) of instrument 128a in a +$X_2$ direction in the instrument workspace in the endoscopic frame. If the user wishes to relinquish control of instrument 128*a* and initiate control of instrument 128*c* using MTM 132*a*, the user registers the indication with the control system 108 and the control of MTM 132*a* is transferred to instrument 128*c*.

FIG. 13 provides one example of a process 250 for controlling a surgical instrument 128*c*, such a uterine elevator instrument, using an inverted mapping technique. Prior to implementation of the inverted mapping technique, the control system 108 will be informed that an inverted mapping technique, rather than a conventional mapping technique is required. This information may be based, for example, on a user input, sensor input, or other feedback identifying the slave instrument or slave arm as arranged in a configuration, such as an end-on view, in which an inverted mapping technique provides more comfortable manipulation for the user. As previously described, an MTM 132 within the master workspace 228 typically has six degrees of freedom, three rotational degrees of freedom and three translational degrees of freedom. The process 250 may be performed with all six degrees of freedom enabled. In an alternative embodiment, the position of the tip of the tissue probe may be mapped without similarly mapping the orientation of the probe. In other words, the rotational/orientation mapping is rendered inoperable. More specifically, the rotational degrees of freedom (yaw, pitch, and roll) may be freed to create an interface that allows the surgeon to perceive that the MTM 132*a* is dragging the tissue probe. Thus, the tissue probe would appear to translate through the three dimensional coordinate system, but rotational capability would be disabled, wherein the rotation of the MTM is locked out. Alternatively, the master rotation may be allowed to float, wherein the rotation is ignored in the transformation of the tissue probe manipulation. In still another alternative, translation is mapped with less than all of the rotational degrees of freedom. For example, translation of the MTM may be mapped with rotation about a Z-axis, without mapping the movement about the X- and Y-axes. Any error between the master and probe with respect to non-active axes may be omitted from display to avoid the need for remapping of the MTM.

At a process 252, movement of a master input device, namely MTM 132*a*, in a first direction in the master workspace 228 is detected. At a process 254, the movement of the MTM 132*a* results in the generation of master control signals. At a process 256, the movement of the MTM 132*a* in the master workspace 228 is mapped to the tissue probe 166 in the instrument workspace. At a process 258, slave control signals are generated to move the tissue probe 166 in the instrument workspace, in an inverted first direction. An inverted direction is reversed or opposite in magnitude along at least one axis of the Cartesian coordinate system. The scale of movement, velocity, and size of the workspace may be controlled based upon the tissue probe used. Limits on the motion of the tissue, e.g. the uterus, may be predetermined and set by the system or by the surgeon's visual cues.

As explained further in the detailed examples provided in FIGS. 14-21, the movement of the master input device in the master workspace may be mapped to instruments in the instrument workspace based upon a determination of the slave instrument insertion direction. For example, if the slave instrument is inserted into the instrument workspace in a direction that corresponds with the direction of the field of view, a mapping associated with the direction of the field of view may be used. Alternatively, if the slave instrument is inserted into the instrument workspace in a direction that is non-corresponding with the direction of the field of view, a different mapping, such as one including an inversion for at least one direction of the slave instrument motion may be used.

A slave instrument insertion direction may be considered "corresponding" based on a geometric relationship between the viewing axis of the imaging instrument and the slave instrument as determined by known kinematic relationship or sensor feedback. A corresponding slave instrument direction may be any direction that is less than or equal to ninety degrees (or, in other embodiments, less than ninety degrees) from the viewing axis (e.g. axis 244). In FIG. 11, instruments 128*a* and 128*b* may be considered to be inserted in a corresponding direction because of their direction relative to the viewing axis 244. A slave instrument direction may also be considered "non-corresponding" based on a geometric relationship between the viewing axis of the imaging instrument and the slave instrument. A non-corresponding slave instrument direction may be any direction that is greater than ninety degrees (or, in other embodiments, no less than ninety degrees) from the viewing axis. In FIG. 11, instrument 128*c* may be considered to be inserted in a non-corresponding direction because of it has an insertion direction approximately 180° from the viewing angle 244 and is not extending between the viewing angle 244 and a plane perpendicular to the distal tip of the imaging instrument 130. Thus in FIG. 11, instruments 128*a*, 128*b* may have a corresponding mapping that corresponds to the field of view along the viewing axis 244, and instrument 128*c* may have a mapping that includes an inversion of the corresponding mapping in at least one direction of motion (e.g., the $X_3$ direction) for the instrument 128*c*. The inversion may be, for example an opposite or 180° change in direction from the corresponding mapping.

Referring now to FIG. 14, the view of the instrument workspace 226 through the endoscope 130, i.e., the endoscopic frame, allows the user at the master console 102 to visualize the section of tissue wall 232, the instrument 128*a* with end effector 129*a*, and the instrument 128*b* with end effector 129*b*. Although the tissue probe 166 in the workspace may not be directly visualized due to the intervening tissue 232, the general location of the tip may be identified by a protrusion, distension, or other quality associated with an area of the tissue 232 that has been elevated by the tip. In one embodiment, an overlay image may be displayed to indicate the location of the tip. This overlay may be triggered when control is switched to the tissue probe. If an imaging probe is used, the tissue may be visualized directly, providing an internal view of the patient anatomy. In this example frame, the $+X_2$ direction is to the right of the page, the $-X_2$ direction is to the left of the page, the $+Y_2$ direction is to the top of the page, the $-Y_2$ direction is to the bottom of the page, the $+Z_2$ direction is out of the page, and the $-Z_2$ direction is into the page. In an alternative embodiment, the surgeon may be primarily interested in the amount of tissue stretch achieved by the probe and will move the probe until the image in the endoscopic frame indicates that the tissue of interest is stretched to the surgeon's specifications.

Referring now to FIG. 15, the probe frame of the instrument workspace 226 from the opposite side of the tissue wall 232 (e.g., from a proximal end of the instrument 128*c*, as viewed from the cervix into the uterus) inverts the X and Z axes as compared to the endoscopic frame ($X_2$, $Y_2$, $Z_2$). Specifically, in this example frame, the $-X_3$ direction is to the left of the page, the $+X_3$ direction is to the right of the page, the $+Y_3$ direction is to the top of the page, the $-Y_3$ direction is to the bottom of the page, the $-Z_3$ direction is into the page, and the $+Z_3$ direction is out of the page.

If the MTM 132a is coupled to move the tissue probe 166, and the surgeon wishes to move the tissue probe 166 toward the location of the end effector 129b, as shown in FIG. 16, he or she moves the MTM 132a in the $+X_4$ direction (toward the MTM 132b in the master space 228). Because of the inverted position (non-corresponding direction) of the instrument 128c, under a conventional, non-inverted mapping scheme, movement of the MTM 132a to the right toward the MTM 132b in the master space 228 would cause the tissue probe 166 in the view of FIG. 17 to also move to the right—in the $+X_3$ direction toward the end effector 129a. To avoid this reversed outcome and to move the tissue probe 166 toward the intended end effector 129b, the mapping of the MTM 132a is inverted. Thus, as shown in FIG. 16, movement of the MTM 132a in the $+X_4$ direction in the master workspace 228 is inverted in the probe frame, causing the tissue probe 166 to move in the $-X_3$ direction (i.e. opposite the $+X_3$ direction), toward the end effector 129b in the endoscopic frame.

More specifically, the control system 108 may be configured to determine if the MTM 132a is communicatively coupled with a slave instrument in a corresponding direction such as an instrument 128a, 128b, 130 (i.e. an instrument other than the tissue probe 166), and if so movement of the MTM 132a in the viewer frame is mapped to movement of the slave instrument in the endoscopic frame according to a first mapping. The first mapping translates movement in a first direction (e.g., to the viewer's right, $+X_4$) in the viewer frame to movement in the first direction (e.g., to the endoscope's right, $+X_2$) in the endoscopic frame. If the MTM 132a is communicatively coupled with a slave instrument in a non-corresponding direction, such as the inverted instrument 128c that includes the tissue probe 166, movement of the MTM 132a in the viewer frame is mapped to movement of the inverted instrument in the probe frame according to a second mapping. The second mapping translates the movement in the first direction (e.g. to the viewer's right, $+X_4$) in the viewer frame to movement in an inverted first direction (e.g. to the tissue probe's left, $-X_3$, as viewed from a proximal location along the shaft of instrument 128c) in the probe frame. The inverted first direction (e.g. $-X_3$) in the probe frame is opposite the first direction (e.g., $+X_4$) in the viewer frame and in the endoscopic frame. In this embodiment, movement of the instrument 128c in the inverted first direction of the probe frame is in the same direction in the instrument workspace as the first direction of the instrument 128a in the endoscopic frame. In other words, in the instrument workspace 226, the first direction $+X_2$ in the endoscopic frame is the same as the inverted first direction $-X_3$ in the probe frame.

Referring now to FIGS. 18 and 19, in another example, a starting position of the tissue probe 166 as in FIGS. 14 and 15 is assumed. If the surgeon wishes to move the tissue probe 166 up, he or she moves the MTM 132a in the $+Y_4$ direction (out of the page in the master space 228 of FIG. 10). In this example, a conventional mapping scheme may be used because an upward movement of the MTM 132a in the master space 228 would cause the tissue probe 166 in the view of FIG. 19 to also move up—in the $+Y_3$ direction. In other words, the "up" movement is the same in both the endoscopic view of FIG. 18 and in the instrument view of FIG. 19. Thus, conventional mapping will result in movement of the tissue probe 166 in the $+Y_2$ direction and the $+Y_3$ direction when the MTM 132a is moved in the $+Y_4$ direction.

More specifically, the control system 108 may be configured to determine if the MTM 132a is communicatively coupled with a slave instrument in a corresponding direction such as an instrument 128a, 128b, 130 (i.e. an instrument other than the tissue probe 166), and if so movement of the MTM 132a in the viewer frame is mapped to movement of the first slave instrument in the endoscopic frame according to a first mapping. The first mapping translates movement in a first direction (e.g., to the viewer's up, $+Y_4$) in the viewer frame to movement in the first direction (e.g., to the endoscope's up, $+Y_2$) in the endoscopic frame. If the MTM 132a is communicatively coupled with a slave instrument in a non-corresponding direction, such as the instrument 128c that includes the tissue probe 166, movement of the MTM 132a in the viewer frame is mapped to movement of the slave instrument in the probe frame according to a second mapping. The second transformation also translates the movement in the first direction (e.g. to the viewer's up, $+Y_4$) in the viewer frame to movement in a first direction (e.g. to the tissue probe's up, $+Y_3$, as viewed from a proximal location along the shaft of instrument 128c) in the probe frame. The first direction (e.g. $+Y_3$) in the probe frame is the same as the first direction (e.g., $+Y_4$) in the viewer frame. In this embodiment, movement of the instrument 128c in the first direction of the probe frame is in the same direction in the instrument workspace as the first direction of the instrument 128a in the endoscopic frame. In other words, in the instrument workspace 226, the first direction $+Y_2$ in the endoscopic frame is the same as the inverted first direction $+Y_3$ in the probe frame.

Referring now to FIGS. 20 and 21, in another example, a starting position of the tissue probe 166 as in FIGS. 14 and 15 is assumed. If the MTM 132a is coupled to move the tissue probe 166 and the surgeon wishes to move the tissue probe 166 away from the tissue wall 232, he or she moves the MTM 132a along the $-Z_4$ direction and away from the viewer of the display system 136 in FIG. 10. Because of the inverted position (non-corresponding direction) of the instrument 128c, under a conventional mapping scheme, movement of the MTM 132a away from the surgeon in the $-Z_4$ direction in the master space 228 would cause the tissue probe 166 in the view of FIG. 21 to move into the page—in the $-Z_3$ direction further into the tissue wall 232. To avoid this reversed outcome and to move the tissue probe 166, as intended, away from the tissue wall 232, the mapping of the MTM 132a is inverted. Thus, as shown in FIG. 20, movement of the MTM 132a in the $-Z_4$ direction in the master workspace 228 is inverted, causing the tissue probe 166 to move in the $+Z_3$ direction (i.e. opposite the $-Z_4$ direction), out of the page and away from the tissue wall 232 (toward the cervix in the probe frame).

More specifically, the control system 108 may be configured to determine if the MTM 132a is communicatively coupled with a slave instrument in a corresponding direction such as an instrument 128a, 128b, 130 (i.e. an instrument other than the tissue probe 166), and if so movement of the MTM 132a in the viewer frame is mapped to movement of the first slave instrument in the endoscopic frame according to a first mapping. The first mapping translates movement in a first direction (e.g., away from the viewer, $-Z_4$) in the viewer frame to movement in the first direction (e.g., away from the endoscope, $-Z_2$) in the endoscopic frame. If the MTM 132a is communicatively coupled with a slave instrument in a non-corresponding direction, such as the instrument 128c that includes the tissue probe 166, movement of the MTM 132a in the viewer frame is mapped to movement of the second slave instrument in the probe frame according to a second mapping. The second mapping translates the movement in the first direction (e.g. away from the viewer, $-Z_4$) in the viewer frame to movement in an inverted first direction (e.g. away from the tissue wall 232, $+Z_3$, as viewed from a proximal location along the shaft of instrument 128c) in the probe frame. The inverted first direction (e.g. $+Z_3$) in the probe frame is opposite the first direction (e.g., $-Z_4$) in the viewer frame and the endoscopic frame. In this embodiment, movement of the instrument 128c in the inverted first direction of the probe frame is in the same direction in the instrument workspace as the first direction of the instrument 128a in the endoscopic frame. In other words, in the instrument workspace 226, the first direction $-Z_2$ in the endoscopic frame is the same as the inverted first direction $+Z_3$ in the probe frame.

Although the examples provided describe linear movements along X, Y, or Z axes, it is understood that angular movements of the MTM 132a in the three dimensional workspace 228 may also be mapped to the three dimensional instrument workspace such that the mapping is inverted as to one or more of the coordinate axes and conventional as to one or more of the coordinate axes. For example, a movement $+X_4$, $+Y_4$, in the viewer and endoscopic frames, may be mapped to correspond to a movement $-X_3$, $+Y_3$, in a probe frame.

The embodiment of FIG. 23 illustrates an alternative slave manipulator system 300. The system 300 includes separate teleoperated manipulator component 302 and manipulator component 304. Both components 302, 304 may be operated via a common master manipulator and control system. Alternatively, they may be operated by different master manipulators, direct manipulators, and/or control systems. Manipulator component 302 is substantially similar to the patient-side manipulator described for FIG. 2, including the surgical instruments that operate under master control. Manipulator component 304 is a separate servo-operated manipulator and includes a mounted instrument 306 with tissue probe 308, similar to any of the embodiments described above. In this embodiment, the manipulator component 304 is mounted to a bed rail 310 of a patient bed 312. The initial positioning of the manipulator component 304 may be performed manually. For example, the manipulator component 304 may be moved along the bed rail 310 and locked in place with a friction locking mechanism. After being locked in place, the manipulator component 304 may be placed under the control of the master manipulator and central control system. With the component 304 locked in position, the mounted instrument 306 with tissue probe 308 may be operated as described for earlier embodiments. In other alternative embodiments, the manipulator component may be mounted on any side of the patient bed or on another movable or stationary component in the surgical arena.

FIGS. 24-26 illustrate an assisting medical instrument 400, such as a uterine elevator, according to another embodiment. For use with teleoperational control, the instrument 400 may be attached to the instrument spar 148 of FIG. 4. The instrument 400 has a proximal end 402 and a distal end 404. The proximal end includes a handle 406 that may be used to manually manipulate the instrument when disconnected from the instrument spar 148. The handle 406 has an ergonomic grip to allow a user to grasp and manipulate the instrument when not under teleoperational control. The instrument 400 further includes a mounting portion 408 sized and shaped to mate with the cannula mount 152. The mounting portion 408 includes a recessed surface 410 that provides identification information indicating characteristics of the instrument such as size and shape. In alternative embodiments, the identification information may be located on a different portion of the instrument. In still other alternative embodiments, the identification information may be read or otherwise sensed at the instrument spar 148 and electronically communicated from the instrument to the control system 108.

The instrument 400 further includes a fixed curved shaft portion 412 having an approximately 90° arc and a fixed radius of curvature. In this embodiment, the curved portion has an arc length. The curved portion 412 and other portions of the instrument 400 may be formed of a rigid material including metals such as stainless steel or titanium, polymers such polyetheretherketone (PEEK), or ceramics. Suitable materials may be light weight but have sufficient strength to resist substantial bending or breaking when a force is applied to the instrument to manipulate tissue in a patient anatomy. The curved portion 412 has a solid shaft but in alternative embodiments may be cannulated to reduce weight or to provide passage for fluid flow or other medical tools.

The distal end 404 of the instrument 400 includes a tip fastener 414 and the curved shaft portion 412 includes channels, grooves, fasteners and other mating features 416. The fastener 414 and mating features 416 are sized and shaped to mate with a medical accessory 418. The medical accessory 418 include a tissue probe 419. The tissue probe 419 may be rounded, flexible, inflatable, and/or have other atraumatic tip characteristics that allow the probe to engage and apply force to tissue without tearing, abrading, or otherwise damaging the tissue. Various medical accessories suitable for use with the instrument 400 are available from CooperSurgical, Inc. of Trumbull, Conn. and may include uterine manipulator accessories from the RUMI® and Koh product lines.

When attached to the instrument spar 148, the instrument 400 may be controlled to pivot about a center of rotation C1 disposed along an axis A1 (perpendicular to the page in FIG. 24) which does not intersect the instrument 400. The instrument 400 may be constrained to single rotational degree of freedom (e.g. pitch). Typically the center of rotation C1 is locked at the patient orifice during surgery and allows for sufficient pitch motion to be available to carry out the intended surgical manipulation. Alternatively, the center of rotation may be located outside of the body to allow a greater range of motion without contacting the patient. Knowledgeable persons will understand that motion around a center of rotation may be constrained by the use of software or by a physical constraint defined by a mechanical assembly.

A location feature 420 is provided on the mounting portion 408 to indicate to a user the direction of the instrument curvature when the curved portion of the instrument is located inside of a patient anatomy and thus is not visible to the user. The location feature 420 may also serve to prevent the instrument 400 from rotating about an axis A2 extending through the mounting portion 408, thus maintaining the center of rotation C1 in a fixed position relative to the instrument spar 148. In this embodiment, the location feature 420 is a projection, but in alternative embodiments may be a marking, a recessed portion or other indicating feature.

During an initial surgical set-up procedure, the instrument 400 is attached to the cannula mount 152. As previously described, instead of a force transmission assembly, a "dummy" force transmission assembly (FIG. 7) can be installed to allow the system to recognize the type of medical instrument attached to the instrument spar. The medical accessory 418 is mated with the curved shaft portion 412 and is coupled to the distal end 404. The assembled instrument 400 is positioned within a body cavity with the tissue probe 419 positioned against a tissue wall of the body cavity. The tissue probe may be, for example, expanded by inflation with a fluid. In an alternative embodiment, the instrument may be positioned through a patient orifice first and then may be coupled to the manipulator after the instrument is in position. As previously described, in various embodiments, the manipulator 140 may be attached to the patient bed, to a movable support structure, or to another fixed or movable component in the surgical area.

In this embodiment, movement of the instrument 400 along the $X_3$ axis (perpendicular to the page in FIG. 24) is restricted and movement of the instrument in the $Y_3$ and $Z_3$ directions is coupled due to the constrained rotational movement of the instrument 400 about the center of rotation C1. For example, as the distal end 404 of the instrument 400 is pivoted forward (clockwise in FIG. 24) about the center of rotation C1 (i.e. a pitch motion about axis A1), the distal end 404 moves in a $+Y_3$, $-Z_3$ direction. As the distal end 404 is pivoted in reverse (counter-clockwise in FIG. 24) about the center of rotation C1, the distal end 404 moves in a $-Y_3$, $+Z_3$ direction. The movement of the MTM 132a that controls the motion of the tissue probe may likewise be coupled in the $Y_1$ and $Z_1$ directions. Alternatively, the movement of the MTM 132a that controls the motion of the tissue probe may be decoupled in the Y1 and Z1 directions. When the movement of the MTM 132a is decoupled, the decoupled movement of the MTM 132a is mapped to approximate MTM movement while accommodating the coupled movement of the instrument.

As an example, if the surgeon wishes to move the tissue probe 419 in the $+Y_3$ direction, he or she moves the MTM 132a along the $+Y_1$ direction (out of the page in the master space 228 of FIG. 10). In this example, a conventional mapping scheme may be used because an upward movement of the MTM 132a in the master space 228 would cause the tissue probe 419 to also move up—in the $+Y_3$ direction. In other words, the "up" movement is the same in both the endoscopic view and in the instrument view. Thus, conventional mapping will result in movement of the tissue probe 419 in the $+Y_3$ direction when the MTM 132a is moved in the $+Y_1$ direction. If the surgeon wishes to move the tissue probe 419 away from the tissue wall 232 (FIG. 11), he or she moves the MTM 132a along the $-Z_1$ direction and away from the surgeon in FIG. 10. Because of the inverted position of the instrument 128c, under a conventional mapping scheme, movement of the MTM 132a away from the surgeon in the $-Z_1$ direction in the master space 228 would cause the tissue probe 419 to move in the $-Z_3$ direction further into the tissue wall. To avoid this reversed outcome and to move the tissue probe 419, as intended, away from the tissue wall 232, the mapping of the MTM 132a is inverted. Thus, movement of the MTM 132a in the $+Z_1$ direction in the master workspace 228 is inverted, causing the tissue probe 166 to move in the $+Z_3$ direction, away from the tissue wall 232 (toward the cervix in the probe frame).

FIGS. 27 and 28 illustrate an assisting medical instrument 450, such as a uterine elevator, according to another embodiment. The medical instrument 450 may be similar in configuration and operation to the instrument 400, with a few distinguishing features as will be described. The medical instrument 450 includes a proximal end 452, a distal end 454, and a curved shaft portion 456 extending between the proximal and distal ends. In this embodiment, a straight shaft portion 458 extends between the proximal end 452 and the curved shaft portion 456. When attached to the instrument spar 148, the instrument 450 may pivot about a center of rotation C2. The straight shaft portion extends the center of rotation C2 away from the spar 148 as compared to the instrument 400. Selection of the proper instrument for use in a particular procedure may be based upon the patient size and the distance between the tissue to be manipulated and natural or surgically created orifice through which the instrument is inserted.

FIG. 29 is a schematic view of an assisting medical instrument 460 that may be mounted to the manipulator 140 of FIG. 4 in a configuration that provides additional degrees of freedom of motion for the tissue probe. In this embodiment, the instrument 460 has a proximal end 462, a distal end 464, a curved shaft portion 466, and a straight shaft portion 468. A tissue probe 469 is mounted to the distal end 464. An axis A3 extends through the straight shaft portion 468. The instrument spar 148 of the manipulator 140 includes an instrument anchor 470. The instrument anchor 470 includes a passageway sized to receive the straight shaft portion 468 to couple instrument 460 to the instrument spar 148. The instrument anchor 470 may be an accessory clamp as described in greater detail in U.S. Pat. No. 8,182,469 (filed Sep. 30, 2005; disclosing "Surgical Accessory Clamp and Method") which is incorporated herein by reference, in its entirety. The instrument anchor 470 may serve as a bearing which permits linear translation of the instrument 460 along the axis A3 and rotational motion of the instrument about the axis A3, while constraining translational motion perpendicular to the axis A3.

A force transmission assembly 472 (substantially similar to force transmission assembly 164 described above) couples actuation forces from actuators in manipulator 140 to move various parts of instrument 460 in order to position and orient the tissue probe 469 mounted at the distal end of the curved shaft 466. A joint 474, such as a quick disconnect mechanism, extends between the proximal and distal ends of the instrument 460. In this embodiment, the joint 474 is between the instrument anchor 470 and the force transmission assembly 472. Alternatively, the joint may extend between the proximal end of the instrument and the force transmission assembly. The joint 474 allows for rotation of the tissue probe 469 about the axis A3 at the joint. The joint 474 may also or alternatively allow for translation of the tissue probe along the axis A3 from the joint. Additionally, the joint 474 permits quick exchange of the distal end of the instrument 460 and the tissue probe 469. For example, joint 474 allows a non-sterile end effector or tissue probe on a distal end of the instrument to be removed from the sterile proximal end portions of the instrument. Furthermore, the joint 474 allows for set-up of the instrument 460 and tissue probe 469 within the patient anatomy without the encumbrance of an attached manipulator. For example, the instrument 460 and tissue probe 469 may be positioned and arranged within the patient body cavity. After this initial set-up activity is complete, the instrument spar 148 with force transmission assembly 472 is introduced to the instrument 460. The straight shaft portion 468 is loaded into the instrument anchor 470, for example, through a distal opening in the instrument anchor or through an opening between pivoting clamp arms. The force transmission assembly 472 may then be operatively coupled to the straight shaft portion via the joint 474. After the instrument 460 is connected to the joint 474, the force transmission assembly 472 is operable to control the rotational movement of the tissue probe 469 about the axis A3 and to control the translation of the tissue probe along the axis A3. In one embodiment, to permit translation of the straight shaft portion 468 relative to the joint, 474, the straight shaft portion between the joint and the curved shaft portion may have a smaller diameter than the straight shaft portion between the joint and the force transmission assembly to permit telescoping motion. The instrument anchor 470 may operate as a bearing to support the rotational and translational motion of the straight portion of the shaft.

FIG. 30 is a schematic view of an assisting medical instrument 480 that may be mounted to the manipulator 140 of FIG. 4 in a configuration that provides additional degrees of freedom of motion for the tissue probe. In this embodiment, the instrument 480 may be substantially similar to the instrument 460 and configuration of FIG. 29 with the differences to be described. In this embodiment, the instrument 480 has a proximal end 482, a distal end 484, a curved shaft portion 486, a straight shaft portion 488, and a tissue probe 490. In this embodiment, a joint 492, such as a quick disconnect joint, is engaged between the distal end 484 and the instrument anchor 470. The joint 492 allows for rotation of the tissue probe 490 and curved portion 486 about the axis A4 at the joint. The joint 492 also allows for translation of the tissue probe along the axis A4 from the joint. Additionally, the joint 492 permits quick exchange of the distal end 484 of the instrument and the tissue probe 490. Furthermore, the joint 492 allows for set-up of the instrument 480 and tissue probe 490 within the patient anatomy without the encumbrance of an attached manipulator. In this embodiment, assembly of the instrument 480 may be less cumbersome that the assembly of the instrument 460 (FIG. 29) because the straight shaft portion may be connected to the joint without the need to feed the straight shaft portion through the instrument anchor. Because the joint 492 is distal of the instrument anchor, the joint should be selected to withstand the tissue probing forces without deformation. With a sufficiently robust joint, the straight shaft portions on either side of the joint may remain generally collinear and aligned with the axis A4. For example, the joint may be capable of withstanding loads of up to approximately 30 lbs.

FIG. 31 is a schematic view of an assisting medical instrument 500 that may be mounted to the manipulator 140 of FIG. 4 in a configuration that provides additional degrees of freedom of motion for the tissue probe. In this embodiment, the instrument 500 may be substantially similar to the instrument 480 and configuration of FIG. 30 with the differences to be described. In this embodiment rather than a quick disconnect joint 474, the instrument 500 has a proximal end 502, a distal end 504, a curved shaft portion 506, a straight shaft portion 508, and a tissue probe 510. In this embodiment, a joint 512, such as a multi-dimensional wrist joint, is between the distal end 504 and the instrument anchor 470. An example of various multi-dimensional wrist joints are described in greater detail in U.S. Pat. No. 6,817,974 (filed Jun. 28, 2002; disclosing "Surgical Tool Having Positively Positionable Tendon Actuated Multi-Disk Wrist Joint") which is incorporated herein by reference, in its entirety. The joint 512 allows for multi-dimensional movement of the tissue probe 510 and curved portion 506. Because the joint 512 is distal of the instrument anchor, the joint should be selected to withstand the tissue probing forces without deformation. With a sufficiently robust joint, the straight shaft portions on either side of the joint remain generally collinear and aligned with the axis A4. For example, the joint may be capable of withstanding loads of up to approximately 30 lbs.

FIG. 32 illustrates an assisting medical instrument 550 including a passive illumination source. The medical instrument 550 may be, for example, a uterine elevator similar to any of the embodiments previously described. For use with teleoperational control, the instrument 550 may be attached to the instrument spar 148 of FIG. 4. The instrument 550 includes a probe portion 552 coupled to a distal end of a shaft portion 554. The probe portion 552 and or the shaft portion 554 may include one or more illumination fiducial markers 556. The illumination fiducial markers 556 may be passive illumination fiducial markers that operate without connection to a power mains or to an energy storage device such as a battery. Passive illumination fiducial markers receive incident light from a light source and in response, emit light. In one alternative, a passive illumination fiducial marker may include a passive light emitting diode (LED) system. A passive LED system may include a photosensor coupled to an LED. The photosensor receives excitation light and generates current to illuminate the LED. In another alternative, a passive illumination fiducial marker may include a well, a channel, a recess, or other cavity or container for containing a fluorescent dye such as indocyanine green (ICG) dye. When the ICG dye is illuminated with light at an excitation wavelength (e.g., about 750 to 800 nm) it may be observed directly or imaged at a longer observation wavelength (e.g., over 800 nm).

Light received from an external source, such as light delivered by an optical fiber to a surgical area, may illuminate the passive marker either directly or through occluding tissue. For example, with reference to FIG. 11, if the passive marker is located on the probe 166 within the body cavity 230 (e.g., a uterus), light emitted from the endoscope 130 may pass through the tissue wall to excite the passive marker on the probe. The excited passive marker emits light that may be visible to a user via the endoscope. Thus, the location of the probe may be recognized, through the occluding tissue, from the light of the passive marker. In alternative embodiments, the excitation light may be supplied by a light source on either the probe side or the end effector side of the tissue wall. In alternative embodiments, the markers may be active illumination fiducial markers, including a battery or other power supply to power an LED or other light source.

FIGS. 33-34 illustrate another example of a medical implement that may be fitted with passive illumination markers. In this embodiment, a colpotomizer cup 560 includes passive illumination markers 562. When used in a medical procedure such as a hysterectomy, the colpotomizer cup 560 may be positioned at the base of a uterus 564. Light from an endoscope 566 or other light source may pass through a wall 568 of the uterus 564 to excite one or more of the markers 562. Light emitted from the excited markers 562 may then be visible through the wall 568 via the endoscope 566. The excited markers 562 may thus serve as a guide for the medical instrument 570 to perform a medical procedure such as an ablation or an incision. For example, if the markers 562 are placed radially around a lip of the cup 560, the ring of markers may serve as a guide for cutting the tissue adjacent to the lip of the cup. Passive markers 574 may also be located on a uterine probe 572, including on an inflatable portion of the probe. Such markers may aid in defining the endometrium and fibroid tumors to allow for safer myomectomy procedures.

Passive markers, such as those described, may be used in a variety of medical procedures to identify instruments, implants, target locations, or leave-behind guides or indicators where occluding tissue would otherwise obstruct direct visualization by an image capture system, a visualization system, or the naked eye.

Although the above described systems and methods are useful for elevating or retracting tissue through natural or surgically created opening in a variety of surgical procedures, they are particularly useful for uterine manipulation.

Uterine manipulation may be used in a hysterectomy procedure or in the treatment of endometriosis to provide constant stable tension to enable precise dissection. Teleoperational control of uterine manipulation may also be particularly useful in cases in which the manual manipulation of a large uterus would lead to user fatigue. In addition to providing tissue tension, uterine manipulators may be used to move the transaction place away from vital structures such as ureters.

Teleoperational uterine manipulation is also useful for improving the surgical autonomy of the console surgeon. The surgeon controls the position exactly to their liking without interacting with or waiting for the patient side assistant. Also, the patient side assistant may be providing surgical assistance instead of holding the manipulator. Teleoperational uterine manipulation may also avoid the patient side assistant from becoming contaminated due to movement between the equipment arms.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A teleoperational system comprising:
   an input device;
   a manipulator configured to couple with and move an instrument; and
   a control system including one or more processors, wherein the control system is configured to:
   in response to a determination that the instrument is inserted into an instrument workspace in a corresponding direction to a field of view of the workspace, map movement of the input device to movement of the instrument according to a first mapping, and
   in response to a determination that the instrument is inserted into the instrument workspace in a non-corresponding direction to the field of view, map movement of the input device to movement of the instrument according to a second mapping, wherein the second mapping includes an inversion of the first mapping for at least one direction of motion of the instrument.

2. The teleoperational system of claim 1, wherein the second mapping includes an inversion of the first mapping for a second direction of motion of the instrument.

3. The teleoperational system of claim 1, wherein the field of view is generated by an imaging instrument in the workspace of the instrument.

4. The teleoperational system of claim 3, wherein the corresponding direction is no more than ninety degrees from a viewing axis of the imaging instrument.

5. The teleoperational system of claim 3, wherein the non-corresponding direction is greater than ninety degrees from a viewing axis of the imaging instrument.

6. The teleoperational system of claim 1, further comprising:
   the instrument, wherein the instrument includes a cannula and a tissue probe mounted to a shaft of the cannula.

7. The teleoperational system of claim 1, further comprising:
   a cannula; and
   the instrument, wherein the instrument includes a transmission assembly component and a shaft separable from the transmission assembly component such that a proximal end of the shaft is insertable through a distal end of the cannula prior to coupling the proximal end of the shaft to the transmission assembly component.

8. The teleoperational system of claim 1, further comprising: the instrument, wherein the instrument includes a tissue probe and wherein the tissue probe includes an imaging device or a passive fiducial marker.

9. The teleoperational system of claim 1, wherein the teleoperational system is a teleoperational medical system, and wherein the teleoperational system further comprises:
   the instrument, wherein the instrument is a medical instrument including a proximal end, a distal end, a rigid curved portion between the proximal and distal ends, and a tissue probe mounted to the distal end and wherein the manipulator is adapted to move the instrument about a center of rotation in response to actuator signals generated by the control system based on the movement of the input device.

10. The teleoperational system of claim 9, wherein the instrument further includes a mounting portion adapted to couple with an instrument anchor of the manipulator, the mounting portion extending between the proximal end and the rigid curved portion.

11. The teleoperational system of claim 1, wherein the manipulator is adapted to move the instrument about a center of rotation in response to actuator signals generated by the control system based on the movement of the input device, and wherein the center of rotation is no coincident with a longitudinal axis extending through the instrument.

12. The teleoperational system of claim 1, wherein the manipulator is adapted to move the instrument about a center of rotation in response to actuator signals generated by the control system based on the movement of the input device, wherein the instrument further includes identification information, and wherein the instrument is movable about the center of rotation in response to the actuator signals generated based upon the identification information.

13. A method comprising:
generating master control signals based on a movement of a master controller in a master workspace;
determining a direction of a field of view of an imaging device in an instrument workspace;
determining whether a slave instrument direction for a slave instrument in the instrument workspace is corresponding to the direction of the field of view or is non-corresponding to the direction of the field of view;
in response to a determination that the slave instrument direction is corresponding to the direction of the field of view, mapping the movement of the master controller to movement of the slave instrument according to a first mapping and generating slave instrument control signals for movement of the slave instrument in the instrument workspace based on the first mapping; and
in response to a determination that the slave instrument direction is non-corresponding to the direction of the field of view, mapping the movement of the master controller to movement of the slave instrument according to a second mapping and generating slave instrument control signals for movement of the slave instrument in the instrument workspace based on the second mapping, wherein the second mapping includes an inversion of the first mapping for at least one direction of motion of the slave instrument.

14. The method of claim 13, wherein the second mapping includes an inversion of the first mapping for a second direction of motion of the slave instrument.

15. The method of claim 13, wherein the slave instrument direction is non-corresponding to the direction of the field of view when the slave instrument direction is greater than ninety degrees from a viewing axis of the imaging device.

16. The method of claim 13, wherein generating the slave instrument control signals for movement of the slave instrument in the instrument workspace based on the second mapping includes generating first control signals for movement of the slave instrument in the at least one direction of motion about a center of rotation, wherein the slave instrument includes a shaft having a proximal end, a distal end, a fixed curved portion between the proximal and distal ends, and a tissue probe mounted to the distal end.

17. The method of claim 13, further comprising receiving identification information from the slave instrument, wherein the slave instrument control signals are generated based upon the identification information.

18. A method of operating a teleoperational instrument system comprising a master input device in a master workspace, an actuated instrument end effector in an instrument workspace, and an actuated tissue probe in the instrument workspace, the method comprising:
generating a set of master control signals in response to movement of the master input device;
responsive to the set of master control signals, generating a first mapping, wherein the first mapping maps the movement of the master input device to movement of the instrument end effector in the instrument workspace;
responsive to the set of master control signals, generating a second mapping, wherein the second mapping maps the movement of the master input device to movement of the actuated tissue probe in the instrument workspace;
in response to a determination that the master input device has control of the actuated instrument end effector, generating a set of instrument control signals using the first mapping; and
in response to a determination that the master input device has control of the actuated tissue probe, generating a set of instrument control signals using the second mapping, wherein the second mapping includes an inversion of the first mapping for at least one direction of motion of the actuated tissue probe.

19. The method of claim 18, wherein generating the set of master control signals includes:
generating a plurality of master control position signals and a plurality of master control rotational signals from the movement of the master input device;
rendering inoperative at least one of the plurality of master control rotational signals to create an operative plurality of master control rotational signals; and
responsive to the plurality of master control position signals and the operative plurality of master control rotational signals, generating the set of instrument control signals for movement of the actuated tissue probe.

20. The method of claim 19, further comprising rendering inoperative all of the plurality of master control rotational signals.

* * * * *

UNITED STATES PATENT AND TRADEMARK OFFICE
CERTIFICATE OF CORRECTION

PATENT NO. : 11,129,683 B2
APPLICATION NO. : 16/316939
DATED : September 28, 2021
INVENTOR(S) : John Ryan Steger et al.

Page 1 of 1

It is certified that error appears in the above-identified patent and that said Letters Patent is hereby corrected as shown below:

In the Claims

Column 25, Claim 11, Line 1, please delete "no coincident" and insert --noncoincident--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*